US007045663B2

(12) United States Patent
Davidson et al.

(10) Patent No.: US 7,045,663 B2
(45) Date of Patent: May 16, 2006

(54) CHIRAL INTEGRIN MODULATORS AND METHODS OF USE THEREOF

(75) Inventors: John B. Davidson, Chicago, IL (US); Alexander V. Tatarintsev, Moscow (RU); Ali S. Turgiev, Moscow (RU); James K. Hildreth, Woodstock, MD (US)

(73) Assignee: Billings Pharmaceuticals, Inc., Chicago, IL (US)

( * ) Notice: Subject to any disclaimer, the term of this patent is extended or adjusted under 35 U.S.C. 154(b) by 114 days.

(21) Appl. No.: 10/332,545

(22) PCT Filed: Jul. 10, 2001

(86) PCT No.: PCT/US01/21826

§ 371 (c)(1),
(2), (4) Date: Jun. 17, 2003

(87) PCT Pub. No.: WO02/04413

PCT Pub. Date: Jan. 17, 2002

(65) Prior Publication Data

US 2004/0053892 A1  Mar. 18, 2004

(51) Int. Cl.
*C07C 321/00* (2006.01)
*A61K 31/105* (2006.01)
*A61K 31/10* (2006.01)

(52) U.S. Cl. ........................ 568/22; 568/23; 514/707; 514/708

(58) Field of Classification Search ................ 568/22, 568/23; 514/707, 708
See application file for complete search history.

(56) References Cited

U.S. PATENT DOCUMENTS

| | | | |
|---|---|---|---|
| 4,126,676 A | 11/1978 | Sanders | 424/98 |
| 4,239,778 A | 12/1980 | Venton et al. | 424/305 |
| 4,274,410 A | 6/1981 | Chvapil | 128/270 |
| 4,341,762 A | 7/1982 | Haast | 424/88 |
| 4,643,994 A * | 2/1987 | Block et al. | 514/165 |
| 4,665,088 A | 5/1987 | Apitz-Castro et al. | 514/420 |
| 4,876,281 A | 10/1989 | Yoshida et al. | 514/517 |
| 5,066,658 A | 11/1991 | Demers et al. | 514/269 |
| 5,093,122 A | 3/1992 | Kodera | 424/195.1 |
| 5,279,941 A | 1/1994 | Lessey | 435/7.21 |
| 5,380,646 A | 1/1995 | Knight et al. | 424/1.69 |
| 5,464,855 A | 11/1995 | Capiris et al. | 514/382 |
| 5,478,725 A | 12/1995 | Lessey | 435/7.21 |
| 5,731,288 A | 3/1998 | Markland, Jr. et al. | 514/12 |
| 5,856,363 A | 1/1999 | Tatarintsev et al. | 514/707 |
| 5,863,954 A | 1/1999 | Tatarintsev et al. | 514/707 |
| 5,863,955 A * | 1/1999 | Tatarintsev et al. | 514/707 |
| 5,932,621 A | 8/1999 | Tatarintsev | 514/707 |
| 5,948,821 A * | 9/1999 | Tatarintsev et al. | 514/707 |
| 5,968,988 A | 10/1999 | Tatarintsev | 514/707 |
| 5,981,602 A * | 11/1999 | Tatarintsev et al. | 514/707 |
| 6,177,475 B1 | 1/2001 | Tatarintsev et al. | 514/707 |

FOREIGN PATENT DOCUMENTS

| | | |
|---|---|---|
| EP | 153881 A2 | 9/1985 |
| EP | 185324 A2 | 6/1986 |
| WO | WO 94/15953 | 7/1994 |

OTHER PUBLICATIONS

Block et al. Antithrombotic Organosulfur Compounds from Garlic: Structural, Mechanistic, and Synthetic Studies. Journal of the American Chemical Society, 1986, vol. 108, p 7045-7055.*
Int'l Search Report for PCT/US01/21826, Oct. 30, 2001, Davidson.
Perbec, L.; Hedqvist, P "Prostaglandins $E_1$ And $E_2$ Antagonize Indomethacin-Induced Decrease In Survival Rate Of Haemorrhagically Shocked Rats," *Acta Chir Scand., suppl.* 1980, 500, 91-94.
Bourinbaiar, A. S.; Nagomy, R. "Human Immunodeficiency Virus Type 1 Infection of Choriocarcinoma-Derived Trophoblasts," *Acta. Virol.*, 1993, 37, 21-28.
Liu, D. Y.; Kaymakcalan, Z. "In Vitro Adgesion Assay," Adhesion: Its Role in Inflammatory Disease, (Harlan, J. M.; Liu, D. Y. eds., W.H. Freeman and Company 1992), *Appendix*, 189-193.
Harlan, J. M.; Winn, R. K.; Vedder, N . B.; Doerschuk, C. M.; Rice, C. L. "In Vivo Models Of Leukocyte Adherence To Endothelium," Adhesion: Its Role in Inflammatory Disease, (Harlan, J. M.; Liu, D. Y. eds., W.H. Freeman and Company 1992), *Chapter 6*, 117-150.
Liu, D. Y.; Harlan, J. M. "Outlook For The Future," Adhesion: Its Role In Inflammatory Disease, (Harlan, J. M.; Liu, D. Y. eds., W.H. Freeman and Company 1992), *Chapter 8*, 183-187.
Levy, J. A. "Viral and Cellular Factors Influencing HIV Tropism," Mechansims and Specificity of HIV Entry into Host Cells, (Dü zgünes, N. ed., Plenum Press 1991), 1-15.
Meyers, K. M. "Pathobiology of Animal Platelets," *Adv. Vet. Sci. Comp. Med.*, 1985, 30, 131-165.
Phillips D. M. "The Role of Cell-to-Cell Transmission in HIV Infection," *AIDS*, 1994, 8, 719-731.
Johnson, V. A. "New Developments In Antiretroviral Drug Therapy for HIV Infection," *AIDS Clinical Review*, 1992, 70-104.

(Continued)

*Primary Examiner*—Sikarl A. Witherspoon
(74) *Attorney, Agent, or Firm*—Brinks Hofer Gilson & Lione; Gregory H. Zayia

(57) ABSTRACT

The invention provides enantiomers of ajoene and derivtives of Z(−)-ajoene. The derivative of Z(−)-ajoene are useful for modulating integrin-mediated functions, for treating disorders, diseases or conditions in which integrins play a role, and for treating tissues to improve their condition for a subsequent use, such as transplantation.

54 Claims, 1 Drawing Sheet

OTHER PUBLICATIONS

Stevenson, M.; Bukrinsky, M.; Haggerty, S. "HIV-1 Replication and Potential Targets for Intervention," *AIDS Res. and Human Retrovir.*, 1992, 8, 107-117.

Butera, S. T.; Folks, T. M. "Application of Latent HIV-1 Infected Cellular Models to Therapeutic Intervention," *AIDS Res. and Human Retrovir.*, 1992, 8, 991-995.

Kolson, D. L.; Buchhalter, J.; Collman, R.; Hellmig, B.; Farrell, C. F.; Debouck, C.; Gonzalez-Scarano, F. "HIV-1 Tat Alters Normal Organization of Neurons and Astrocytes in Primary Rodent Brain Cell Cultures: RGD Sequence Dependence," *AIDS Res. and Retrovir.*, 1993, 9, 677-685.

Guo, M. M. L.; Hildreth J. E. K. "HIV Acquires Functional Adhesion Receptors from Host Cells," *Aids Research And Human Retroviruses*, 1995, 11, 1007-1013.

Hsueh, W.; Gonzalez-Crussi, F.; Arroyave, J. L. "Platelet-Activating Factor-Induced Ischemic Bowel Necrosis," *AJP*, 1986, 122, 231-239.

Acosta, E. P.; Fletcher, C. V. "Agents for Treating Human Immunodeficiency Virus Infection," *Am. J. Hosp. Pharm.*, 1994, 51, 2251-2267.

Zutter, M. M.; Mazoujian, G.; Santoro, S. A. "Decreased Expression Of Integrin Adhesive Protein Receptors In Adenocarcinoma Of The Breast," *American Journal Of Pathology*, 1990, 137, 863-870.

Feuerstein, G.; Hallenbeck, J. M. "Prostaglandins, Leukotrienes, and Platelet-Activating Factor in Shock," *Am. Rev. Pharmacol. Toxicol.*, 1987, 27, 301-313.

Bone, Roger C. "The Pathogenesis of Sepsis," *Annals of Internal Medicine*, 1991, 115, 457-469.

Henderson, W. R. "The Role of Leukotrienes in Inflammation," *Ann. Intern. Med.*, 1994, 121, 684-697.

Mueller, B. M.; Reisfeld, R. A.; Silveira, M. H.; Duncan, J. D.; Wrasidlo, W. A. "Pre-Clinical Therapy of Human Melanoma with Melanoma with Morpholino-Doxorubicin Conjugated to a Monoclonal Antibody Directed Against an Integrin on Melanoma Cells," *Antibody, Immunoconjugates, and Radiopharmaceuticals*, 1991, 4, 99-106.

Tadi, P. P.; Lau, B. H. S.; Teel, R. W.; Hermann, C. F. "Binding of Aflatoxin $B_1$ to DNA by Ajoene and Diallyl Sulfide," *Anticancer Research*, 1991, 11, 2037-2042.

Chambers, A. F.; Behrend, E. I.; Wilson, S. M.; Denhardt, D. T. "Induction of Expression of Osteopontin (OPN; Secreted Phosphoprotein) in Metastatic, Ras-Transformed, NIH 3T3 Cells," *Anticancer Research*, 1992, 12, 43-48.

Delaha, E. C.; Garagusi, V. F. "Inhibition of Mycobacteria by Garlic Extract (*Allum sativum*)," *Antimicrob. Agents Chemother.*, 1985, 27, 485-486.

San-Blas, G.; San-Blas, F.; Gil, F.; Marino, L.; Apitz-Castro, R. "Inhibition of Growth of the Dimorphic Fungus *Paracoccidioides brasiliensis* by Ajoene," *Antimicrobial Agents and Chemotherapy*, 1989, 33, 1641-44.

Perez, H. A.; De La Rosa, M.; Apitz, R. "In Vivo Activity of Ajoene against Rodent Malaria," *Antimicrobial Agents and Chemotherapy*, 1994, 38, 337-339.

Bridges, C. G.; Brennan, T. M.; Taylor, D. L.; McPherson, M.; Tyms, A. S. "The Prevention of Cell Adhesion and the Cell-to-Cell spread of HIV-1 In Vitro by the α-glucosidase 1 Inhibitor, 6-obutanoyl Castanospermine (MDL 28574)," *Antiviral Research*, 1994, 25, 169-175.

Yoshida, S.; Kasuga, S.; Hayashi, N.; Ushiroguchi, T.; Matsuura, H.; Nakagawa, S. "Antifungal Activity of Ajoene Derived from Garlic," *Applied and Environmental Microbiology*, 1987, 53, 615-17.

Nock, L. P.; Mazelis, M. "The C-S Lyases of Higher Plants: Preparation and Properties of Homogeneous Alliim Lyase from Garlic (*Allium sativum*)," *Archives of Biochemistry and Biophysics*, 1986, 249, 27-33.

Hite, L. A.; Jia, L-G.; Bjamason, J. B.; Fox, J. W. "cDNA Sequences for Four Snake Venom Metalloproteinases: Structure, Classification, and Their Relationship to Mammalian Reproductive Proteins," *Archives of Biochemistry and Biophysics*, 1994, 308, 182-191.

Kavanaugh, A. F.; Davis, L. S.; Nichols, L. A.; Norris, S. H.; Rothlein, R. Scharschmidt, L. A.; Lipsky P. E. "Treatment of Refractory Rheumatoid Arthritis With a Monoclonal Antibody to Intercellular Adhesion Molecule 1," *Arthritis & Rheumatism*, 1994, 37, 992-999.

Oelkers, B.; Diehl, H.; Liebig, H. "In Vitro Inhibition of Cytochrome P-450 Reductases from Pig Liver Microsomes by Garlic Extracts," *Arzneim.-Forsch/Drug Res.*, 1992, 42, 136-39.

Bordia, A. "Effect of Garlic on Human Platelet Aggregation In Vitro," *Atherosclerosis*, 1978, 30, 355-60.

Bachelot, C.; Cano, E.; Grelac, F.; Saleun, S.; Druker, B. J.; Levy-Toledano, S.; Fischer, S.; Rendu, F. "Functional Implications of Tyrosine Protein Phosphorylation in Platelets," *Biochem J.*, 1992, 284, 923-28.

Huang, T-F.; Sheu, J-R.; Teng, C-M. "A Potent Antiplatelet Peptide, Triflavin, From Trimeresurus Flavoviridis Snake Venom," *Biochem J.*, 1991, 277, 351-357.

Zhuang, Q.; Stracher, A. "Purification and Characterization of a Calcium Binding Protein With 'Synexin-Like' Activity From Human Blood Platelets," *Biochem. Biophys. Res. Commun.*, 1989, 159, 236-241.

Gargouri, Y.; Moreau, H.; Jain, M. K.; de Haas, G. H.; Verger, R. "Ajoene Prevents Fat Digestion by Human Gastric Lipase In Vitro," *Biochemica et Biophysica Acta*, 1989, 1006, 137-39.

Apitz-Castro, R.; Jain, M. K.; Bartoli, F.; Ledezma, E.; Ruiz, M-C.; Salas, R. "Evidence for Direct Coupling of Primary Agonist-Receptor Interaction to the Exposure of Functional IIb-IIIa Complexes in Human Blood Platelets. Results from Studies with the Antiplatelet Compound Ajoene," *Biochemica et Biophysica Acta*, 1991, 269-80.

Rendu, F.; Daveloose, D.; Debouzy, J. C.; Bourdeau, N.; Levy-Tolendano, S.; Jain, M. K.; Apitz-Castro, R. "Ajoene, the Antiplatelet Compound Derived from Garlic, Specifically Inhibits Platelet Release Reaction by Affecting the Plasma Membrane Internal Microviscosity," *Biochemical Pharmacology*, 1989, 38, 1321-28.

Huang,T-F.; Liu, C-Z.; Ouyang, C.; Teng, C-M. "Halysin, an Antiplatelet Arg-Gly-Asp-Containing Snake Venom Peptide, As Fibrinogen Receptor Antagonist," *Biochemical Pharmacology*, 1991, 42, 1209-1219.

Chen, Y.; Pitzenberger, S. M.; Garsky. V. M.; Lumma, P. K.; Sanyal, G.; Baum, J. "Proton NMR Assignments and Secondary Structure of the Snake Venom Protein Echistatin," *Biochemistry*, 1991, 30, 11625-11636.

Calvete, J. J.; Schäfer, W.; Soszka, T.; Lu, W.; Cook, J. J.; Jameson, B. A.; Niewiarowski, S. "Identification of the Disulfide Bond Pattern in Albolabrin, an RGD-Containing Peptide from the Venom of Trimersurus Albolabris: Significance for the Expression of Platelet Aggregation Inhibitory Activity," *Biochemistry*, 1991, 30, 5225-5229.

Saudek, V.; Atkinson, R. A.; Pelton, J. T. "Three-Dimensional Structure of Echistatin, the Smallest Active RGD Protein," *Biochemistry*, 1991, 20, 7369-7372.

Hite, L. A.; Shannon, J. D.; Bjamason, J. B.; Fox, J. W. "Sequence of a cDNA Clone Encoding the Zinc Metalloproteinase Hemorrhagic Toxin e from *Crotalus atrox*: Evidence for Signal, Zymogen, and Disintegrin-like Structures," *Biochemistry*, 1992, 31, 6203-6211.

Adler, M.; Carter, P.; Lazarus, R. A.; Wagener, G. "Cysteine Pairing in the Glycoprotein IIbIIIa Antagonist Kistrin Using NMR, Chemical Analysis, and Structure Calculations," *Biochemistry*, 1993, 32, 282-289.

Adler, M.; Wagner, G. "Sequential $^1$H NMR Assignments of Kristin, a Potent Platelet Aggregation Inhibito and Glycoprotein IIb-IIIa Antagonist", *Biochemistry*, 1992, 31, 1031-1039.

Blood, C. H.; Zetter, B. R. "Tumor Interactions with the Vasculature: Angiogenesis and Tumor Metastasis," *Biochim. Biophys. Acta*, 1990, 1032, 89-118.

Sud'ina, G. F.; Tatarintsev, A. V.; Koshkin, A. A.; Zaitsev, S. V.; Fedorov, N. A.; Varfolomeev, S. D. "The Role of Adhesive Interactions and Extracellular Matrix Fibronectin from Human Polymorphonuclear Leukocytes in the Respiratory Burst," *Biochimica et Biophysica Acta*, 1991, 1091, 257-60.

Rucinski, B.; Niewiarowski, S.; Holt, J. C.; Soszka, T.; Knudsen, K. A. "Batroxostatin, an Arg-Gly-Asp-containing Peptide from Bothrops Atrox, is a Potent Inhibitor of Platelet Aggregate and Cell Interaction with Fibronectin," *Biochimica et Biophysica Acta*, 1990, 1054, 257-262.

Huang, T. F.; Wang, W-J.; Teng, C-M.; Ouyang, C. "Mechanism of Action of the Antiplatelet Peptide, Arietin, From Bitis Arietans Venom," *Biochimica et Biophysica Acta*, 1991, 1074, 144-150.

Huang, T. F.; Wang, W-J.; Teng, C-M.; Liu, C-S.; Ouyang, C. "Purification and Characterization of an Antiplatelet, Arietin, from Bitis Arietans Venom", *Biochimica et Biophysica Acta*, 1991, 1074, 136-143.

Giancotti, F. G.; Mainiero, F. "Integrin-Mediated Adhesion and Signaling In Tumorigenesis," *Biochimica et Biophysica Acta*, 1994, 1198, 47-64.

Williams, J.; Rucinski, B.; Holt, J. "Elagantin and Albolabrin Purified Peptides From Viper Venoms; Homologies With the RGDS Domain of Fibrinogen and Von Willebrand Factor," *Biochimica et Biophysica Acta*, 1990, 1039, 81-89.

Dedhar, S. "Integrins and Tumor Invasion," *BioEssays*, 1990, 12, 583-590.

Bronson, R. A.; Fusi, F. "Evidence that an Arg-Gly-Asp Adhesion Sequence Plays a Role in Mammalian Fertilization," *Biol. Reprod.*, 1990, 43, 1019-1025.

Pearce-Pratt, R.; Phillips, D. M. "Studies of Adhesion of Lymphocytic Cells: Implications for Sexual Transmission of Human Immunodeficiency Virus," *Biology of Reproduction*, 1993, 48, 431-445.

Phillips, D. R.; Charo, I. F.; Parise, L. V.; Fitzgerald, L. A. "The Platelet Membrane Glycoprotein IIb-IIa Complex," *Blood*, 1988, 71, 831-43.

Yarchoan, R.; Pluda, J. M.; Perno, C-F.; Mitsuya, H.; Broder, S. "Anti-Retroviral Therapy of Human Immunodeficiency Virus Infection: Current Strategies and Challenges for the Future," *Blood*, 1991, 78, 859-884.

Wake, A.; Tanaka, Y.; Nakatsuka, K.; Misago, M.; Oda, S.; Morimoto, I.; Eto, S. "Calcium-Dependent Homotypic Adhesion Through Leukocyte Function-Associated Antigen-1/Intracellular Adhesion Molecule-1 Induces Interleukin-1 And Parathyroid Hormone-Related Protein Production on Adult T-Cell Leukemia Cells In Vitro," *Blood*, 1995, 86, 2257-2267.

Brodt, P.; Fallavolita, L.; Sawka, R. J.; Shibata, P.; Nip, J.; Kim, U.; Shibata, H. "Tumor Cell Adhesion to Frozen Lymph Node Sections —a Correlate Of Lymphatic Metastasis in Breast Carcinoma Models of Human and Rat Origin," *Breast Cancer Research and Treatment*, 1990, 17, 109-120.

Hart, I. R.; Birch, M.; Marshall, J. F. "Cell Adhesion Receptor Expression During Melanoma Progression and Metastasis," *Cancer and Metastasis Rev.*, 1991, 10, 115-128.

Kramer, R. H.; Vu, M.; Cheng, Y-F.; Ramos, D. M. "Integrin Expression in Malignant Melanoma," *Cancer and Metastasis Rev.*, 1991, 10, 49-59.

Brodt, P. "Adhesion Mechanisms in Lymphatic Metastasis," *Cancer and Metastasis Reviews*, 1991, 10, 23-32.

Hermann, G. G.; Geertsen, P. F.; Von Der Maase, H.; Zeuthen, J. "Interleukin-2 Dose, Blood Monocyte And CD25+ Lymphocyte Counts as Predictors of Clinical Response to Interleukin-2 Therapy in Patients with Renal Cell Carcinoma," *Cancer Immunology Immunotherapy*, 1991, 34, 111-114.

Scharfenberg et al., *Cancer Letters*, 1990, 53, 103-08. The cytotoxic effect of ajoenem a natural product from garlic.

Kramer, R. H.; McDonald, K. A.; Crowley, E.; Ramos, D. M.; Damsky, C. H.; "Melanoma Cell Adhesion to Basement Membrane Mediated by Integrin-related Complexes," *Cancer Res.*, 1989, 49, 393-402.

Sumiyoshi, H.; Wargovich, M. J. "Chemoprevention of 1,2-Dimethylhydrazine-induced Colon Cancer in Mice by Naturally Occurring Organosulfur Compounds," *Cancer Res.*, 1990, 50, 5084-5087.

Trikha, M.; De Clerck, Y. A.; Markland, F. S. "Contortrostatin, a Snake Venom Disintegrin, Inhibits $\beta_1$ Integrin-Mediated Human Metastic Melanoma Cell Adhesion and Blocks Experimental Metastasis," *Cancer Research*, 1994, 54, 4993-4998.

Schreiner, C.; Fisher, M.; Hussein, S.; Juliano, R. L. "Increased Tumorigenicity of Fibronectin Receptor Deficient Chinese Hamster Ovary Cell Variants," *Cancer Research*, 1991, 51, 1738-1740.

Mortarini, R.; Gismondi, A.; Santoni, A.; Parmiani, G.; Anichini, A. "Role Of The $\alpha_5\beta_1$ Integrin Receptor in the Proliferative Response of Quiescent Human Melanoma Cells to Fibronectin," *Cancer Research*, 1992, 52, 4499-4506.

Witjes, M.; Scholma, J.; van Drunen, E.; Roodenburg, J. L. N.; Mesander, G.; Hagemeijer, A.; Tomson, A. M. "Characterization of a Rat Oral Squamous Cell Carcinoma Cell Line UHG-RaC '93 Induced by 4-Nitroquinoline-1-Oxide In Vivo," *Carcinogenesis*, 1995, 16, 2825-2832.

Taichman, D. B.; Cyblsky, M. I.; Djaffar, I.; Longenecker, B. M.; Teixido, J.; Rice, G. E.; Aruffo, A.; Bevilacqua, M. P. "Tumor Cell Surface $\alpha^4\beta_1$ Integrin Mediates Adhesion to Vascular Endothelium: Demonstration of an Interaction with the N-Terminal Domains of INCAM-110/VCAM-1," *Cell Regulation*, 1991, 2, 347-355.

Kramer, R. H.; Vu, M. P.; Cheng, Y-F.; Ramos, D. M.; Timpl, R.; Waleh, N. "Laminin-Binding Integrin $\alpha_7\beta_1$: Functional Characterization and Expression in Normal and Malignant Melanocytes," *Cell Regulation* , 1991, 2, 805-817.

Hermanowski-Vosatka, A.; Van Strijp, J. A. G.; Swiggard, W. J.; Wright S. D. "Integrin Modulating Factor-1: A Lipid that Alters the Function of Leukocyte Integrins," *Cell*, 1992, 68, 341-52.

Hynes, R. O. "Integrins: Versatility, Modulation, and Signaling in Cell Adhesion," *Cell*, 1992, 69, 11-25.

Plantefaber, L. C.; Hynes, R. O. "Changes In Integrin Receptor on Oncogenically Transformed Cells," *Cell*, 1989, 56, 281-290.

Bishop, J. M. " Molecular Themes In Oncogenesis," *Cell*, 1991, 64, 235-248.

Bourinbaiar, A. S.; Nagomy, R. "Effect of Serine Protease Inhibitor, N-α-Tosyl-L-lysyl-Chloromethyl Ketone (TLCK), on Cell-Mediated and Cell-Free HIV-1 Spread," *Cellular Immunology*, 1994, 155, 230-236.

Qian, Y. X.; Shen, P. J.; Xu, R. Y.; Liu, G. M.; Yang, H. Q.; Lu, Y. S.; Sun, P.; Zhang, R. W.; Qi, L. M.; Lu, Q. H. "13095s Spermicidal Effect In Vitro by the Active Principle of Garlic," *Chem. Abstracts*, 1987, 106, 95.

Saeed, S. A.; Khan, M. A. S.; Khan, S. "Differential Inhibition of Arachidonate Cyclo-Oxygenase and Lipoxygenase Enzymes by Drugs and New Approaches to Anti-Inflammatory Therapy," *Chem. Abstracts*, 1987, 107, 400435.

Delaha, E. C.; Garagusi, V. F. "218177j Inhibition of Mycobacteria by Garlic Extract (*Allium Sativum*)," *Chem. Abstracts*, 1985, 102, 351.

Lichtenstein, L. M.; Pickett, W. C. "45756h Treatment of Allergies and Inflammatory Conditions," *Chem. Abstracts*, 1986, 104, 55.

Wagner, W.; Kessler, H.; Husemann, B "The Effect of Subcutaneous Nitrosamine Injections on the Origin of Tumors of the Liver and Their Inhibition by Vitamin C," *Chem. Abstracts*, 1988, 413645.

Mohr, E. "54653g The Composition of Fermented Garlic Powder," *Chem. Abstracts*, 1988, 108, 602.

Nakagawa, S.; Kasuga, S.; Matsuura, H. "Prevention of Liver Damage by Aged Garlic Extract and Its Components in Mice," *Chem. Abstracts*, 1989, 111, 146760e.

Belman, S.; Solomon, J.; Segal, A.; Block, E.; Barany, G. "Inhibition of Soybean Lipoxygenase and Mouse Skin Tumor Promotion by Onion and Garlic Components," *Chem. Abstracts*, 1990, 112, 91227.

Sumiyoshi, H.; Wargovich, M. J. "Chemoprevention of 1,2-dimethylhydrazine-Induced Colon Cancer in Mice by Naturally Occurring Organosulfur Compounds," *Chem. Abstracts*, 1990, 113, 126061r.

Dausch, J. G.; Nixon, D.; W. "Garlic: A Review of Its Relationship to Malignant Disease," *Chem. Abstracts*, 1990, 113, 1840408c.

Meng, C. L.; Shyu, K. W.; "Inhibition of Experimental Carcinogenesis by Painting with Garlic Extract," *Chem. Abstracts*, 1991, 115, 43950v.

Tadi, P.P.; Lau, B. H. S.; Teel, R. W.; Herrmann, C. E. "187586z Binding of Aflatoxin $B_1$ to DNA Inhibited by Ajoene and Diallyl Sulfide," *Chem. Abstracts*, 1992, 116, 26.

Soma, G.; Yoshimura, K.; Tsukioka, D.; Mizuno, D.; Oshima, H. "Macrophage-Activating Lipopolysaccharide (LPS) as Antiherpes Agents and Veterinary Antiherpes Agent," *Chem. Abstracts*, 1992, 116, 76349e.

Demers, J. P.; Sulsky, R. B. "Preparation of Hydroxyureas as 5-lipoxygenase and Cyclooxygenase Inhibitors," *Chem. Abstracts*, 1992, 116, 128198.

Perez, H.; De La Rosa, M.; Apitz, R. "In Vivo Activity of Ajoene Against Rodent Malaria," *Chem. Abstracts*, 1994, 120, 182454c.

Sabata, S.; Moshonov, S.; Zor, U.; Floman, Y.; Nzor, Z. "Lipoxygenase Inhibitor and Colchine as Anti-Arthritic Agents in the Rats," *Chem. Abstracts*,1986, 508135.

Nishikawa, Y.; Fukukawa, T.; Utsumi, K.; Sasae, Y.; Hayami, T. "30034j Effect of Vitamin $B_1$ (Thiamine) Derivatives on Motility and Viability of Bull and Goat Spermatozoa," *Chem. Abstracts*, 1971, 74, 172.

Nakata, T. "Effect of Fresh Garlic Extract on Tumor Growth," *Chem. Abstracts*, 1973, 79, 111680x.

Shah, S. A.; Vohora, S. B. "204565z Boron Enhances Anti-Arthitic Effects of Garlic Oil," *Chem. Abstracts*, 1990, 113, 32.

Tsai, Y.; Cole, L. L.; Davis, L. E.; Lockwood, S. J.; Simmons, V.; Wild, G. C. "61572a Antiviral Properties of Garlic: In Vitro Effects on Influenza $B_1$ Herpes Simplex and Coxsackie Viruses," *Chemical Abstracts*, 1986, 104, 24.

Rendu, F.; Daveloose, D.; Debouzy, J. C.; Bourdeau, N.; Levy-Toledano, S.; Jain, M. K.; Apitz-Castro, R. "Ajoene, the Antiplatelet Compound Derived From Garlic, Specifically Inhibits Platelet Release Reaction by Affecting the Plasma Membrane Internal Microviscosity," *Chemical Abstracts*, 1989, 111, abstract No. 464.

Hub, E.; Middleton, J.; Rot, A. "Mechanism of Chemokine-Induced Leukocyte Adhesion And Emigration," Chemoattractant Ligands and Their Receptors, (Horuk, R. ed., CRC Press 1996) Chapter 13, 301-325.

Coller, Barry S.; Folts, J. D.; Smith, S. R.; Scudder, L. E.; Jordan, R. "Abolition of In Vivo Platelet Thrombus Formation in Primates with Monoclonal Antibodies to the Platelet GPPIIb/IIIa Receptor: Correlation with Bleeding Time, Platelet Aggregation, and Blockade of GPIIb/IIIA Receptors," *Circulation*, 1989, 80, 1766-1774.

Mousa, S. A.; Bozarth, J. M.; Forsythe, M. S.; Jackson, S. M.; Leamy, A.; Diemer, M. M.; Kapil, R. P.; Knabb, R. M.; Mayo, M. C.; Pierce, S. K.; De Grado, W. F.; Thoolen, M. J.; Reilly, T. M. "Antiplatelet and Antithrombotic Efficacy of DMP 728, a Nove Platelet GPIIb/IIIa Receptor Antagonist," *Circulation*, 1994, 89, 3-12.

Tcheng, J. E.; Ellis, S. G.; George, B. S.; Kereiakes, D. J.; Kleiman, N. S.; Talley, J. D.; Wang, A. L.; Weisman, H. F.; Califf, R. M.; Topol, E. J. "Pharmacodynamics of Chimeric Glycoprotein IIb/IIIa Integrin Antiplatelet Antibody Fab 7E3 in High-Risk Coronary Angioplasty," *Circulation* , 1994, 90, 1757-1764.

Shebuski, R. J.; Stabilito, I. J.; Sitko, G. R.; Polokoff, M. H. "Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis," *Circulation*, 1990, 82, 169-177.

Thöme, L. J.; Jönsson, B-A.; Norgren, L.; Strand, S-E. "Effect Of Ticlopidine and Prostaglandin E on Endotoxin-Induced Pulmonary Platelet Sequestration In Vivo," *Circulatory Shock*, 1986, 20, 61-69.

Svartholm, E.; Bergqvist, D.; Lindblad, B.; Ljungberg, J.; Haglund, U. "Pulmonary Vascular Response to Live *Escherichia Coli*. Influences of Different Antiplatelet Substances," *Circulatory Shock*, 1987, 22, 173-183.

Svartholm, E.; Bergqvist, D.; Haglund, U.; Ljungberg, J.; Hedner, U. "Coagulation and Fibrinolytic Reactions in Experimental Porcine Septic Shock: Pretreatment with Different Antiplatelet Factors," *Circulatory Shock*, 1987, 22, 291-301.

Tracey, K. j. "Tumor Necrosis Factor (Cachectin) in the Biology of Septic Shock Syndrome," *Circulatory Shock*, 1991, 35, 123-128.

Fleckenstein, A. E.; Smith, S. L.; Linseman, K. L.; Beuving, L. J.; Hall, E. D. "Comparison of the Efficacy of Mechanistically Different Antioxidants in the Rat Hemorrhagic Shock Model," *Circulatory Shock*, 1991, 35, 223-230.

Palmer, S.; Hablin, A. S. "Increased CD11/CD18 Expression on the Peripheral Blood Leucocytes of Patients with HIV Disease: Relationship to Disease Severity," *Clin, Exp. Immunol.*, 1993, 93, 344-349.

Locher, C. H.; Vanham, G.; Kestens, L.; Kruger, M.; Ceuppens, J. L.; Vingerhoets, J. "Expression Patterns of Fc-γ Receptors, HLA-DR and Selected Adhesion Molecules on Monocytes from Normal and HIV-Infected Individuals," *Clin. Exp. Immunol.*, 1994, 98, 115-122.

Gehlsen, K. R.; Davis, G. E.; Sriramarao, P. "Integrin Expression in Human Melanoma Cells With Differing Invasive and Metastic Properties," *Clin. Exp. Metastasis*, 1992, 10, 111-120.

Haming, R.; Myers, C.; Merluzzi, V. J. "Monoclonal Antibodies to Lymphocyte Function-Associated Antigen-1 Inhibit Invasion of Human Lymphoma and Metastasis of Murine Lymphoma," *Clin. Exp. Metastasis*, 1993, 11, 337-342.

Nishikawa, T.; Fukukawa, T.; Utsumi, K.; Sasae, Y.; Hayami, T. "Effect of Vitamin $B_1$ (Thiamine) Derivatives on Motility and Viability of Bull and Goat Spermatozoa,"0 *Cong. Intern Reprod. Anim. Insem. Artif., Paris*, 1968, 2,1287-1289.

Qian, Y. X.; Shen, P. J.; Xu, R. Y.; Liu, G. M.; Yang, H. Q.; Lu, Y. S.; Sun, P.; Zhang, R. W.; Qi, L. M..; Lu, Q. H. "Spermicidal Effect In Vitro by the Active Principle of Garlic," *Contraception*, 1986, 34, 295-302.

Juliano, R. L.; Varner, J. A. "Adhesion Molecules in Cancer: The Role of Integrins," *Current Opinion In Cell Biology*, 1993, 5, 812-818.

Pantaleo, G.; Fauci, A. S. "Tracking HIV During Disease Progression," *Current Opinion in Immunology*, 1994, 6, 600-604.

Mohan, P. "Problems and Perspectives in the Design of Anti-HIV-1 Agents," *Drug Development Research*, 1993, 29, 1-17.

Ohta, H.; Tsurudome, M.; Matsumura, H.; Koga, Y.; Morikawa, S.; Kawano, M.; Kusugawa, S.; Komada, H.; Nishio, M.; Ito, Y. "Molecular and Biological Characterization of Fusion Regulatory Proteins (FRPs): anti-FRP mAbs Induced HIV-Mediated Cell Fusion Via an Integrin System," *The EMBO Journal*, 1994, 13, 2044-2055.

Debouzy, J.-C.; Neumann, J.-M.; Hervé, M.; Daveloose, D.; Viret, J.; Apitz-Castro, R. "Interaction of Antiaggregant Molecule Ajoene with Membranes," *European Biophysics Journal*, 1989, 17, 211-16.

Mazur, P.; HEnzel, W. J.; Seymour, J. L.; Lazurus, R. A. "Ornatins: Potent Glycoprotein IIb-IIIa Antagonists and Platelet Aggregation Inhibitors From the Keech Placobdella Ornata," *Eur. J. Biochem*, 1991, 202, 1073-1082.

Dalvit, C.; Widmer, H.; Bovermann, G.; Breckenridge, R.; Metternich, R. "$^1$H NMR Studies of Echistatin in Solution—Sequential Resonance Assignments and Secondary Structure," *Eur. J. Biochem*, 1991, 202, 315-321.

Cooke, R. M.; Carter, B. G.; Martin, D. M. A.; Murray-Rust, P.; Weir, M. P. "Nuclear Magnetic Resonance Studies of the Snake Toxin Echistatin $^1$H Resonance Assignments and Secondary Structure," *Eur. J. Biochem*, 1991, 202, 323-328.

Saudek, V.; Atkinson, R. A.; Lepage, P.; Pelton, J. T. "The Secondary Structure of Echistatin from $^1$H-NMR, Circular-Dichroism and Raman Spectroscopy," *Eur. J. Biochem*, 1991, 202, 329-338.

Falanga, P. B.; Butcher, E. C. "Late Treatment with Anti-LFA-1 (CD11a) Antibody Prevents Cerebral Malaria in a Mouse Model," *Eur. J. Immunol.*, 1991, 21, 2259-2263.

Grau, G. E.; Pointaire, P.; Piguet, P-F.; Vesin, C.; Rosen, H.; Stamenkovic, I.; Takei, F.; Vassalli, P. "Late Administration of Monoclonal Antibody to Leukocyte Function-Antigen 1 Abrogates Incipient Murine Cerebral Malaria," *Eur. J. Immunol.*, 1991, 21, 2265-2267.

Huitinga, I.; Damioseaux, J. G. M. C.; Döpp, E. A.; Dijkstra, C. D. "Treatment with Anti-CR3 Antibodies ED7 and ED8 Suppresses Experimental Allergic Encephalomyelitis in Lewis Rats," *Eur. J. Immunol.*, 1993, 23, 709-715.

Butini, L.; De Fougerolles, A. R.; Vaccarezza, M.; Graziosi, C.; Cohen, D. I.; Montroni, M.; Springer, T. A.; Pantaleo, G.; Fauci, A. S. "Intracellular Adhesion Molecules (ICAm)-1 ICAM-2 and ICAM-3 Function as Counter-Receptors for Lymphocyte Function-Associated Molecule 1 in Human Immunodeficiency Virus-Mediated Syncytia Formation," *Eur. J. Immunol.*, 1994, 24, 2191-2195.

Knudsen, K. A.; Tuszynski, G. P.; Huang, T-F.; Niewiarowski, S. "Trigramin, an RGD-Containing Peptide from Snake Venom, Inhibits Cell-Substratum Adhesion of Human Melanoma Cells," *Experimental Cell Research*, 1988, 179, 42-49.

Soszka, T.; Knudsen, K. A.; Beviglia, L.; Rossi, C.; Poggi, A.; Niewiarowski, S. "Inhibition of Murine Melanoma Cell-Matrix Adhesion and Experimental Metastasis by Albolabrin, an RGD-Containing Peptide Isolated from the Venom of Trimeresurus albolabris," *Experimental Cell Research*, 1991, 196, 6-12.

Falconi, R.; Cimino, L.; Gentileschi, M. P.; D'Agnano, I.; Zupi, G.; Kennel, S. J.; Sacchi, A. "Expression of β1, β3, β4. and β5 Integrins by Human Lung Carcinoma Cells of Different Histotypes," *Exp. Cell Res.*, 1994, 210, 113-122.

Majda, J. A.; Gerner, E. W.; Vanlandingham, B.; Gehlsen, K. R.; Cress, A. E. "Heat Shock-Induced Shedding of Cell Surface Integrins in A549 Human Lung Tumor Cells in Culture," *Exp. Cell Res.*, 1994, 210, 46-51.

Mitsuya, H.; Yarchoan, R.; Kageyama, S.; Broder, S. "Targeted Therapy of Human Immunodeficiency Virus-Related Disease," *The FASEB Journal*, 1991, 5, 2369-2381.

Smole, S.; Harper, W.; Trial, J.; Laughter, A.; Rossen, R. HIV-1 Tat Protein Stimulates LFA-1/CAM-1 Dependent Homotypic Aggregation of Uinfected Monocytoid Cells, FASEB J., 1992, 6, A1714.

Focke, M.; Feld, A.; Lichtenthaler, H. K. "Allicin, A Naturally Occuring Antibiotic from Garlic, Specifically Inhibits Acetl-CoA Synthetase," *FEBS Letters*, 1990, 261, 106-08.

Calvete, J. J.; Wang, Y.; Mann, K.; Schafer, W.; Niewiarowski, S.; Stewart, G.J. "The Disulfide Pattern of Snake Venom Distintegrins, Flavoridin and Echistatin," *FEBS Letters*, 1992, 309, 316-320.

Shah, S. A.; Vohora, S. B. "Boron Enhances Anti-Arthritic Effects of Garlic Oil," *Fitoterapia*, 1990, 61, 121-6.

Mohr, *Gordian*, 1989, 87, 195-196.

Mazzone, A.; Ricevuti, G. "Leukocyte CD11/CD18 Integrins: Biological and Clinical Relevance," *Haematologica*, 1995, 80, 161-175.

Bianchi, A.; Omedé, P.; Attisano, C.; Camponi, A.; Dianzani, U.; Boccadoro, M.; Pileri, A.; Massaia, M. "Phenotypic and Functional Analysis of Peripheral Blood Lymphocytes During Interferon-Alpha 2b Therapy in Multiple Myeloma Patients with Low Tumor Mass," *Haematologica*, 1991, 76, 383-388.

Asselot-Chapel, C.; Salvat, S.; Clayette, P.; Leblond, V.; Raoul, H.; Mabondzo, A.; Lafuma, C.; Dormont, D. "PO-A12 Cellular Factors in Viral Replication: PO-A12-0207 HIV1 Infection of Macrophages Results in Modulation of Fibronectin and $\alpha\beta 1$ Integrin Biosynthesis," *IX International Conference on AIDS*, 1993, 169.

Kalter, D. C.; Gendelman, H. E.; Meltzer, M. S. "Inhibition of Human Immunodeficiency Virus Infection in Monocytes by Monoclonal Antibodies Against Leukocyte Adhesion Molecules," *Immunol. Letters*, 1991, 30, 219-228.

Patarroyo, M.; Prieto, J.; Rincon, J.; Timonen, T.; Lundberg, C.; Lindhom, L.; Asjo, B.; Gahmberg, C. G. "Leukocyte-Cell Adhesion: A Molecular Process Fundamental in Leukocyte Physiology," *Immunol. Rev.*, 1990, 67-108.

Larson, R. S.; Springer, T. A. "Structure and Function of Leukocyte Integrins," *Immunological Reviews*, 1990, 114, 181-216.

Carlos, T. M.; Harlan, J. M. "Membrane Proteins Involved in Phagocyte Adherence to Endothelium," *Immunological Reviews*, 1990, 114, 5-28.

Ikeda, N.; Mukaida, N.; Kaneko, S.; Fujioka, N.; Su, S-B.; Nariuchi, H.; Unoura, M.; Harada, K-I.; Nakanuma, Y.; Kobayashi, K-I.; Matsushima, K. "Prevention of Endotoxin-Induced Acute Lethality in *Propionibacterium acnes*-Primed Rabbits by an Antibody to Leukocyte Integrin $\beta_2$ with Concomitant Reduction of Cytokine Production," *Infection and Immunity*, 1995, 63, 4812-4817.

Ogata, M.; Matsumoto, T.; Kamochi, M.; Yoshida, S-I.; Mizguchi, Y.; Shigematsu, A. "Protective Effects of a Leukotriene Inhibitor and a Leukotriene Antagonist On Endotoxin-Induced Mortality In Carrageenan-Pretreated Mice," *Infection And Immunity*, 1992, 60, 2432-2437.

Simon, R. H.; Ward, P. A. "Adult Respiratory Distress Syndrome," Inflammation: Basic Principles and Clinical Correlates, 2nd Ed., (Gallin, J. I.; Goldstein, I. M.; Snyderman, R. eds., Raven Press Ltd., 1992), Chapt. 51, 999-1016.

Kishimoto, T. K.; Anderson, D. C. "The Role of Integrins in Inflammation," Inflammation: Basic Principles and Clinical Correlates, 2nd Ed., (Galin, J. I.; Goldstein, I. M.; Snyderman, R. eds., Raven Press Ltd., 1992), Chapter 20, pp. 353-406.

Hardan, I.; Weiss, L.; Hershkowitz, R.; Greenspoon, N.; Alon, R.; Cahalon, L.; Reich, S.; Slavin, S.; Lider, O. "Inhibition of Metastatic Cell Colonization in Murine Lungs and Tumor-Induced Morbidity by Nonpeptidic ARG-GLY-ASP Mimetics," *Int. J. Cancer*, 1993, 55, 1023-1028.

Van Muijen, G. N. P.; Jansen, K. F. J.; Cornelissen, I. M. H. A.; Smeets, D. F. C. M.; Beck, J. L. M.; Ruiter, D. J. "Establishment and Characterization of a Human Melanoma Cell Line (MV3) Which is Highly Metastatic in Nude Mice," *Int. J. Cancer*, 1991, 48, 85-91.

Tang, G.; Onoda, J. M.; Steinert, B. W.; Grossi, I. M.; Nelson, K. K.; Umbarger, L.;Diglio, C. A.; Taylor, J. D.; Honn, K. V. "Phenotypic Properties of Cultured Tumor Cells: Integrin $\alpha_{IIb}\beta_3$ Expression, Tumor-Cell-Induced Platelet Aggregation, and Tumor-Cell Adhesion to Endothelium as Important Parameters of Experimental Metastasis," *Int. J. Cancer*, 1993, 54, 338-347.

Krief, P.; Saint-Ruf, C.; Bracke, M.; Boucheix, C.; Billard, C.; Billard, M.; Cassingena, R.; Jasmin, C.; Mareel, M. and Azzarone, B. "Aquisition of Tumorigenic Potential in the Human Myoepithelial HBL100 Cell Line is Associated with Decreased Expression of HLA Class I, Class II and Integrin $\beta 3$ and Increased Expression of *c-myc*," *Int. J. Cancer*, 1989, 43, 658-664.

Ishizuka, M.; Kawatsu, M.; Yamashita, T.; Ueno, M.; Takeuchi, T. "Low Molecular Weight Immunomodulators Produced by Microorganisms," *Int. J. Immunopharmacol.*, 1993, 17, 133-139.

Watanabe, S-i.; Mukaida, N.; Ikeda, N.; Akiyama, M.; Harada, A.; Nakanishi, I.; Nariuchi, H.; Watanabe, Y. Matsushima, K. "Prevention of Endotoxin Shock by an Antibody Against Leukocyte Integrin $\beta 2$ Through Inhibiting Production and Action of TNF," *International Immunology*, 1995, 7, 1037-1046.

Glander, H.-J.; Schaller, J. "Beta 1-Integrins of Spermatozoa: a Flow Cytophotometric Analysis," *International Journal of Andrology*, 1993, 16, 105-111.

Ramos, D.M.; Cheng, Y. F.; Kramer, R. H. "Role of Laminin-Binding Integrin in the Invasion of Basement Membrane Matrices by Fibrosarcoma Cells," *Invasion Metastasis*, 1991, 11, 125-138.

Reinhardt, P. P.; Heaton, R. K.; McCutchen, J. A.; Wallace, M. A.; Grant, I.; Spector, S. A. "PO-A14-0285 Neurocognitive Disorder is Associated with High Replicating, Syncytia Inducing HIV-1 Isolates In Cerebrospinal Fluid," *IX International Conference On AIDS*, 1993, 182.

Kawaguchi et al. *Jpn. J. Cancer Res.*, 1992, 83, 1304-1316.
Fujita et al. *Jpn. J. Cancer Res.*, 1992, 83, 1317-26.
Murata et al. *Jpn. J. Cancer Res.*, 1992, 83:1327-1333.

Sheu, J. R.; Lin, C. H.; Chung, J. L.; Teng, C. M.; Huang, T. F. "Triflavin, an Arg-Gly-Asp-Containing Antiplatelet Peptide Inhibits Cell-Substratum Adhesion and Melanoma Cell-Induced Lung Colonization," *Jpn. J. Cancer Res.*, 1992, 83, 885-893.

Belman, S.; Solomon, J.; Segal, A. "Inhibition of Soybean Lipoxgenase and Mouse Skin Tumor Promotion by Onion and Garlic Components," *Journal of Biochemical Toxicology*, 1989, 4, 151-60.

Freeman, F.; Kodera, Y. "Garlic Chemistry Stability of S-(2-Propenyl 2-Propene-1-sulfinothioate (Allicin) in Blood, Solvents, and Simulated Physiological Fluids," *J. Agric. Food Chem.*, 1995, 43, 2332-38.

Block, E.; Ahmad, S.; Jain, M. K.; Crecely, R. W.; Apitz-Castro, R.; Cruz, M. R. "(E,Z)-Ajoene: A Potent Antithrombotic Agent From Garlic," *J. Am. Chem. Soc.*, 1984, 106, 8295-96.

Block, E.; Ahmad, S.; Catalfamo, J. L.; Jain, M. K.; Apitz-Castro, R. "Antithrombotic Organosulfur Compounds from Garlic: Structral, Mechanistic, and Synthetic Studies," *J. Am. Chem. Soc.*, 1986, 108, 7045-55.

Huang, T-F.; Sheu, J-R.; Teng, C-M.; Chen, S-W.; Liu, C-S. "Triflavin, an Antiplatelet Arg-Gly-Asp-Containing Peptide, is a Specific Antagonist of Platelet Membrane Glycoprotein IIb-IIIa Complex," *j. Biochem*, 1991, 109, 328-334.

Takeya, H.; Nishida, S.; Nishino, N.; Makinose, Y.; Omori-Satoh, T.; Nikai, T.; Sugihara, H.; Iwanaga, S. "Primary Structures of Platelet Aggregation Inhibitors (Disintegrins) Autoproteolytically Released from Snake Venom Hemorrhagic Metalloproteinases and New Fluorogenic Peptide Substrates for These Enzymes," *J. Biochem*, 1993, 113, 473-483.

Yamakawa, Y.; Omori-Satoh, T.; Maeyama, J-i. "Primary Structures of Cytotoxic Factors Isolated from Habu (*Trimeresurus Flavoviridis*) Venom," *J. Biocem.*, 1991, 109, 667-669.

Cheresh, D. A.; Spiro, R. C. "Biosynthetic and Functional Properties of an Arg-Gly-Asp-directed Receptor Involved in Human Melanoma Cell Attachment to Vitronectin, Fibrinogen, and von Willebrand Factor," *J. Biol. Chem.*, 1987, 262, 17703-17711.

Savage et al., "Binding of the Snake Venom-Derived Proteins Applagin and Echistan to the Arginine-Glycine Aspactic Acid Recognition Platelet Glycoprotein IIb-IIIa Complex Inhibits Receptor Function," *The Journal of Biological Chemistry*, 1990, 265, 11766-11772.

Mould, A. P.; Komoriya, A.; Yamada, K. M.; Humphries, M. J. "The CS5 Peptide is a Second Site in the IIICS Region of Fibronectin Recognized by the Integrin $\alpha_4\beta_1$," *The Journal of Biological Chemistry*, 1991, 266, 3579-3585.

Takeya et al., *The Journal of Biological Chemistry*, 1992, 267, 14109-14117.

Gan, et al., "Echistatin, A Potent Platelet Aggregation Inhibitor From the Venom of the Viper, *Echis Carinatus*", *The Journal of Biological Chemistry*, 1988, 263, 19827-19832.

Huang, et al., "Trigramin, A Low Molecular Weight Peptide Inhibiting Fibrinogen Interaction With Platelet Receptors Expressed on Glycoprotein IIb-IIIA Complex," *The Journal of Biological Chemistry*, 1987, 262, 16157-16163.

Shebuski et al., "Characterization and Platelet Inhibitory Activity of Bitistatin, a Potent Arginine-Glycine-Aspartic Acid-containing Peptide from the Venom of the Viper Bitis arietans," *The Journal of Biological Chemistry*, 1989, 264, 21550-21556.

Seymour et al., "Decorsin—A Potent Glycoprotein IIb-IIIa Antagonist and Platelet Aggregation Inhibitor From the Leech Macrobdella Decora," *The Journal of Biological Chemistry*,1990, 265, 10143-10147.

Takeya, et al., "The Complete Amino Acid Sequence of the High Molecular Mass Hemorrhagic Protein HR1B Isolated from the Venom of *Trimeresurus flavoviridis*," *The Journal of Biological Chemistry*, 1990, 265, 16068-16073.

Scarborough, et al., "Barbourin—A GPIIb-IIIa-Specific Integrin Antagonist From the Venom of Sistrurus *M. Barbouri*," *The Journal of Biological Chemistry*, 1991, 266, 9359-9362.

Paine et al., "Purification, Cloning, and Molecular Characterization of a High Molecular Weight Hemorrhagic Metalloprotease, Jararhagin, from Bothrops Jararaca Venom," *The Journal of Biological Chemistry*, 1992, 267, 22869-22876.

Scarborough, R. M.; Rose, J. W.; Naughton, M. A.; Phillips, D. R.; Nannizzi, L.; Arfsten, A.; Campbell, A. M.; Charo, I. F. " Characterization of the Integrin Specificities of Disintegrins Isolated from American Pit Viper Venoms," *The Journal of Biological Chemistry*, 1993, 268, 1058-1065.

Scarborough et al., "Design of Potent and Specific Integrin Antagonists," *The Journal of Biological Chemistry*, 1993, 268, 1066-1073.

Roossien, F. F.; de Rijk, D.; Bikker, A.; Roos, E. "Involvement of LFA-1 in Lymphoma Invation and Metastasis Demonstrated with LFA-1-deficient Mutants," *J. Cell. Biol.*, 1989, 108, 1979-83.

Brake, D. A.; Debouck, C.; Biesecker, G. "Identification of an Arg-Gly-Asp (RGD) Cell Adhesion Site in Human Immunodeficiency Virus Type 1 Transactivation Protein, tat," *J. Cell Biol.*, 1990, 111, 1275.

Sato, M.; Sardana, M. K.; Grasser, W. A.; Garsky, V. M.; Murray, J. M.; Gould, R. J. "Echistatin Is a Potent Inhibitor of Bone Resorption in Culture," *Journal of Cell Biology*, 1990, 111, 1713-1723.

Weeks, B. S.; Klotman, M. E.; Dhawan, S.; Kibbey, M.; Rappaport, J.; Kleinman, H. K.; Yamada, K. M.; Klotman, P. E. "HIV-1 Infection of Human T Lymphocytes Results in Enhanced $\alpha_5\beta_1$ Integrin Expression," *J. Cell. Bio.*, 1991, 114, 847-853.

Vogel, B. E.; Lee, S-J.; Hildebrand, A., Craig, W.; Pierschbacher, M. D.; Wong-Stal, F.; Ruoslahti, E. "A Novel Integrin Specificity Exemplified by Binding of the $\alpha_v\beta_5$ Integrin to the Basic Domain of the HIV Tat Protein and Vitronectin," *J. Cell Biol.*, 1993, 121, 461.

Knudsen, K. A.; Smith, L.; Smith, S.; Karczewski, J.; Tuszynski, G. P. "Role of IIb-IIIa-Like Glycoproteins in Cell-Substratum Adhesion of Human Melanoma Cells," *J. Cell. Physiol.*, 1988, 136, 471-78.

Ramachandrula, A.; Tiku, K.; Tiku, M. L. "Tripeptide RGD-Dependent Adhesion of Articular Chondrocytes to Synoval Fibroblasts," *Journal Of Cell Science*, 1992, 101, 859-871.

Mochizuki, E.; Nakayama, A. "Liquid Chromatographic Determination of Alliin in Garlic and Garlic Products," *Journal of Chromatography*, 1988, 455, 271-77.

Yu, T-H.; Wu, C.M. "Effects of pH on the Formation of Flavour Compounds of Disrupted Garlic," *Journal of Chromatography*, 1989, 462, 137-45.

Stevens, J. H.; O'Hanley, P.; Shapiro, J. M.; Mihm, F. G.; Satoh, P. S.; Collins, J. A.; Raffin, T. A. "Effects of Anti-C5a Antibodies on the Adult Respiratory Distress Syndrome in Septic Primates," *J. Clin Invest.*, 1986, 77, 1812-1816.

Hsiao, L. L.; Peltonen, J.; Jaakkola, S.; Gralnick, H.; Uitto, J. "Plasticity of Integrin Expression by Nerve-Derived Connective Tissue Cells," *J. Clin Invest.*, 1991, 87, 811-820.

Humphries, M.J., yamada, K. M.; Olden, K. "Investigation of the Biological Effects of Ani-Cell Adhesive Synthetic Peptides that Inhibit Experimental Metastasis of B16-F10 Murine Melanoma Cells," *J. Clin. Invest.* 1988, 81, 782-790.

Vedder, N. B.; Winn, R. K.; Rice, C. L.; Chi, E. Y.; Arfors, K.-E.; Harlan, J. M. "A Monoclonal Antibody to the Adherence-promoting Leukocyte Glycoprotein, CD18, Reduces Organ Injury and Improves Survival from hemorrhagic Shock and Resuscitation in Rabbits," *J. Clin. Invest.*, 1988, 81, 939-944.

Felding-Habermann, B.; Mueller, B. M.; Romerdahl, C. A.; Cheresh, D. A. "Involvement of Integrin $\alpha V$ Gene Expression in Human Melanoma Tumorigencity," *J . Clin. Invest.*, 1992, 89, 2018-2022.

Nip, J.; Shibata, H.; Loskutoff, D. J.; Cheresh, D. A.; Brodt, P. "Human Melanoma Cells Derived from Lymphatic Metastases Use Integrin $\alpha_v\beta_3$ to Adhere to Lymph Node Vitronectin," *J. Clin. Invest.*, 1992, 90, 1406-1413.

Fletcher, C. V.; Acosta, E. P. "Advances in Pharmacotherapy: Treatment of HIV Infection," *Journal of Clinical Pharmacy and Therapeutics*, 1993, 18, 375-388.

Yarchoan, R.; Broder, S. "Correlations Between the *In Vitro* and *In Vivo* Activity of Anti-HIV Agents: Implications for Future Drug Development," *J. Enzyme Inhibition*, 1992, 6, 99-111.

Pantaleo, G.; Butini, L.; Graziosi, C.; Poli, G.; Schnittman, S. M.; Greenhouse, J. J.; Gallin, J. I.; Fauci, A. S. "Human Immunodeficiency Virus (HIV) Infection in CD4+ T Lymphocytes Genetically Deficient in LFA-1: LFA-1 is Required for HIV-mediated Cell Fusion but not for Viral Transmission," *J. Exp. Med.*, 1991, 173:511-514.

Issekutz, A. C.; Issekutz, T. B. "Monocyte Migration to Arthritis in the Rat Utilizes Both Cd11/CD18 and Very Late Activation Antigen 4 Integrin Mechanisms," *J. Exp. Med.*, 1995, 181, 1197-1203.

Issekutz, T. B.; Miyasaka, M.; Issekutz, A. C. "Rat Blood Neutrophils Express Very Late Antigen 4 and It Mediates Migration to Arthritic Joint and Dermal Inflammation," *J. Exp. Med.*, 1996, 183, 2175-2184.

Postigo, A. A.; Corbi, A. L.; Sá nchez-Madrid, F.; de Landázuri, M. O. "Regulated Expression and Function of CD11c/CD18 Integrin on Human B Lymphocytes. Relation Between Attachment to Fibrinogen and Triggering of Proliferation Through CD11c/CD18," *J. Exp. Med.*, 1991, 174, 1313-1322.

Meerloo, T.; Sheikh, M. A.; Bloem, A. C.; de Ronde, A.; Schutten, M.; van Els, C. A. C.; Roholl, P. J. M.; Joling, P.; Goudsmit, J.; Schuurman, H-J. "Host Cell Membrane Proteins on Human Immunodeficiency Virus Type 1 After In Vitro Infection of H9 Cells and Blood Mononuclear Cells. An Immuno-Electron Microscopic Study," *J. Gen. Virol.*, 1993, 74, 129-135.

Chehimi, J.; Prakash, K.; Shanmugam, V.; Collman, R.; Jackson, S. J.; Bandyopadhyay, S.; Starr, S. E. "CD4-Independent Infection of Human Peripheral Blood Dendritic Cells with Isolates of Human Immunodefiecncy Virus Type 1," *Journal of General Virology*, 1993, 74, 1277-1285.

Kazazi, F.; Chang, J.; Lopez, A.; Vadas, M.; Cunningham, A. L. "Interleukin 4 and Human Immundeficiency Virus Stimulate LFA-1-ICAM-1-Mediated Aggregation of Monocytes and Subsequent Giant Cell Formation," *Journal of General Virology*, 1994, 75, 2795-2802.

Valentin, A.; Lundin, K.; Patarroyo, M.; Asjo, B. "The Leukocyte Adhesion Glycoprotein CD18 Participates in HIV-1-Induced Syncytia Formation in Monocytoid and T Cells," *J. Immunol.*, 1990, 144, 934-937.

Zahalka, M. A.; Okon, E.; Naor, D. "Blocking Lymphoma Invasiveness with a Monoclonal Antibody Directed Against the β-Chain of the Leukocyte Adhesion Molecule (CD18)," *J. Immunol.*, 1993, 150, 4446-4477.

Guo, M. M. L.; Hildreth, J. E. K. "HIV-Induced Loss of CD 44 Expression in Monocytic Cell Lines," *J. Immunol.*, 1993, 151, 2225-2236.

Broaddus, V. C.; Boylan, A. M.; Hoeffel, J. M.; Kim, K. J.; Sadick, M.; Chuntharapai, A.; Hébert "Neutralization of IL-8 Inhibits Neutrophil Inlux in a Rabbit Model of Endotoxin-Induced Pleruisy," *Journal of Immunology*, 1994, 152, 2960-2967.

Tabata, N.; Ito, M.; Shimokata, K.; Suga, S.; Ohgimoto, S.; Tsurudorne, M.; Kawano, M.; Matsumura, H.; Komada, H.; Nishio, M.; Ito, Y. "Expression of Fusion Regulatory Proteins (FRPs) on Human Peripheral Blood Monocytes," *J. Immunol.*, 1994, 153, 3256-3266.

Denis, M. "Tat Protein from HIV-1 Binds to *Micobacterium avium* Via a Bacterial Integrin," *The Journal of Immunology*, 1994, 153, 2072-2081.

VanOtteren, G. M.; Steiner, R. M.; Kunkel, S. L.; Paine III, R.; Greenberger, M. J.; Danforth, J. M.; Burdick, M. D.; Standiford, T. J. "Compartmentalized Expression of RANTES in a Mrine Model of Endotoxemia," *The Journal of Immunology*, 1995, 154, 1900-1908.

Bukowski, R. M.; Sergi, J. S.; Budd, G. T.; Murthy, S.; Tubbs, R.; Gibson, V.; Bauer, L.; Stanley, J.; Guatam, S.; Finke, J. "Phase I Trial of Continuous Infusion Interleukin-2 and Doxorubicin in Patients with Refractory Malignancies," *Journal of Immunotherapy*, 1991, 10, 432-439.

Olive, D.; Lopez, M.; Blaise, D.; Viens, P.; Stoppa, A-M.; Brandely, M.; Mawas, C.; Mannoni, P.; Maraninchi, D. "Cell Surface Expression of ICAM-1 (CD54) And LFA-3 (CD58), Two Adhesion Molecules, is Up-Regulated on Bone Marrow Leukemic Blasts After In Vivo Administration of High-Dose Recombinant Interleukin-2," *Journal of Immunotherapy*, 1991, 10, 412-417.

Mirelman et al., *The Journal of Infectious Diseases*, 1987, 156, 243-44.

Shenep, J. L.; Mogan, K. A. "Kinetics of Endotoxin Release During Antibiotic Therapy For Experimental Gram-Negative Bacterial Sepsis," *The Journal of Infectious Diseases*, 1984, 150, 380-388.

Stent, G.; Cameron, P. U.; Crowe, S. M. "Expression of CD11/CD18 and ICAM-1 on Monocytes and Lymphocytes of HIV-1-Infected Individuals," *Journal of Leulocyte Biology*, 1994, 56, 304-309.

Birdsall, H. H.; Trial, J.; Hallum, J. A.; de Jong, A. L.; Green, L. K.; Bandres, J. C.; Smole, S. C.; Laughter, A. H.; Rossen, R. D. "Phenotypic and Functional Activation of Monocytes in HIV-1 Infection: Interactions with Neural Cells," *Journal of Leukocyte Biology*, 1994, 56, 310-317.

Mukaida, N.; Ishikawa, Y.; Ikeda, N.; Fujioka, N.; Watanabe, S-i.; Kuno, K.; Matsushima, K. "Novel Insight into Molecular Mechanism of Endotoxin Shock: Biochemical Analysis of LPS Receptor Signaling in a Cell-Free System Targeting NF-κB and Regulation of Cytokine Production/Action Through $\beta_2$ Integrin In Vivo," *Journal of Leukocyte Biology*, 1996, 59, 145-151.

Sheu, J. R.; Lin, C. H.; Huang, T. F. "Triflavin, an Antiplatelet Peptide, Inhibits Tumor Cell-Extracellular Matrix Adhesion Through an Arginine-Glycine-Aspartic Acid-Dependent Mechanism," *J. Lab. Clin. Med.*, 1994, 123, 256-263.

Ziegler, S. J.; Sticher, O. *Journal of Liquid Chromatography*, 1989, 12, 199-220.

Ugen, K. E.; Mahalingam, M.; Klein, P. A.; Kao, K-J. "Inhibition of Tumor Cell-Induced Platelet Aggregation and Experimental Tumor Metastasis by the Syntheic Cly-Arg-Gly-Asp-Ser Peptide," *J. Natl. Cancer Inst.*, 1988, 80, 1461-1466.

Pignatelli, M.; Hanby, A. M.; Stamp, G. W. H. "Low Expression of $\beta_1$, $-\alpha_1$ and $-\alpha_3$ Subunits of VLA Integrins in Malignant Mammary Tumors," *Journal of Pathology*, 1991, 165, 25-32.

Saeed, S. A.; Khan, M. A. S.; Khan; S. "Differential Inhibition of Arachidonate Cyclo-Oxy-Genase and Lipoxygenase Enzymes by Drugs and New Approaches to Anti-Inflammatory Therapy," *J. Pharm.*, 1985, 6, 77-82.

Terashita, Z-I.; Imura, Y.; Shino, A.; Nishikawa, K. "A Lethal Role of Platelet Activating Factor in Ananphylactic Shock in Mice," *The Journal of Pharmacology and Experimental Therapeutics*, 1987, 243, 378-383.

Douglas, G. C.; Hu, J.; Thirkill, T. L.; Hovanes, K.; Sharma, S.; King, B. F. "Effect of Cytokines and Anti-Adhesion Molecule Antibodies on the Adhesion of Lymphocytic Cells to Human Synctiotrophoblast," *Journal of Reproductive Immunology*, 1994, 24, 49-62.

Buchanan, S. A.; Mauney, M. C.; deLima, N. F.; Binns, O. A. R.; Cope, J. S.; Shockey, K. S.; Gordon, S. G.; Erwin, M. B.; Sutherland, G.; Kron, I. L.; Tribble, C. G. "Enhanced Isolated Lung Function After Ischemia with Anti-Intercellular Adhesion Molecule Antibody," *J. Thorc. Cardiovasc. Surg*, 1996, 111, 941-7.

Ito, Y.; Komada, H.; Kusagawa, S.; Tsurudome, M.; Matsumura, H.; Kawano, M.; Ohta, H.; "Fusion Regulation Proteins on the Cell Surface: Isolation and Characterization of Monoclonal Antibodies which Enhance, Giant Polykaryocyte Formation in Newcastle Disease Virus-Infected Cell Lines of Human Origin," *Journal of Virology*, 1992, 66, 5999-6007.

Schuitemaker, H.; Koot, M.; Kootstra, N. A.; Dercksen, M. W.; de Goede, R. E. Y.; van Steenwijk, R. P.; Lange, J. M. A.; Eeftink Schattenkerk, J. K. M.; Miedema, F.; Tersmette, M. "Biological Phenotype of Human Immunodeficiency Virus Type 1 Clones at Different Stages of Infection: Progression of Disease is Associated with a Shift from Monocytotropic to T-Cell Tropic Virus Populations," *Journal of Virology*, 1992, 66, 1354-1360.

Bai, M.; Campisi, L.; Freimuth, P. "Victronectin Receptor Antibodies Inhibit Infection of HeLa and A549 Cells by Adenovirus Type 12 but Not by Adenovirus Type 2," *J. Virol.*, 1994, 68, 5925-5932.

Karamov, E. V.; Kornilayeva, G. V.; Makarova, T. V.; Tatarintsev, A. V.; Vrzheshch, P. V.; Schegolev, A. A.; Yershov, D. E.; Fedorov, N. A.; Turgiev, A. S. "Cytotoxic Effect of Ajoene on Neoplastic T-Cells is Possibly Related to its Action on Integrins," Keystone Symposia on Molec. & Cell. Biol., Conference Abstract, Apr. 4, 1992.

Tatarinstev, A. V.; Vrzheshch, P. V.; Schegolev, A. A.; Saprylina, N. A.; Kozlov, A. M. "Ajoene Inhibits Experimental Metastasis and Implantation of Melanoma Cells in Mice," Keystone Symposia on Molec. & Cell. Biol., Conference Abstract, Apr. 4, 1992.

Kellermann, W.; Frentzel-Beyme, R.; Welte, M.; Jochum, M. "Phospholipase A in Acute Lung Injury After Trauma and Sepsis: Its Relation to the Inflammatory Mediators PMN-Elastase, C3a, and Neopterin," *Klin Wochenschr*, 1989, 67, 190-195.

Vink et al., *Lab Invest.*, 1993, 68, 192-203.

Aboulker, J-P. "Preliminary Analysis of the Concorde Trial," *The Lancet*, 341, 889-890.

Horst, E.; Radaszkiewicz, T.; Hooftman-den Otter, A.; Pieters, R.; van Dongen, J. J. M.; Meijer, C. J. L. M.; Pals. S. T. "Expression of the Leucocyte Integrin LFA-1 (CD11a/CD18) and Its Ligand ICAM-1 (CD54) in Lymphoid Malignancies is Related to Lineage Derivation And Stage of Differentiation but Not to Tumor Grade," *Leukemia*, 1991, 5, 848-853.

Kortlepel, K.; Bendall, L. J.; Gottlieb, D. J. "Human Acute Myeloid Leukemia Cells Express Adhesion Proteins and Bind to Bone Marrow Fibroblast Monolayers And Extracellular Matrix Proteins," *Leukemia*, 1993, 7, 1174-1179.

Altieri, D. C.; Bader, R.; Mannucci, P. M.; Edgington, T. S. "Oligospecificity of the Cellular Adhesion Receptor MAC-1 Encompasses an Inducible Recognition Specificity for Fibrinogen," *Leukocyte Fibrinogen Receptor*, 1988, 1893-1900.

Reynolds-Kohler, C.; Wiley, C.; Nelson, J. A. "Cells Infected by Human Immunodeficiency Virus In Vivo," *Mechanisms and Specificity of HIV Entry Into Host Cells*, 1991, 27-44.

Lewis, R. A.; Austen, K. F.; Soberman, R. J. "Leukotrienes and Other Products of the 5-Lipoxygenase Pathway," *Mechanisms of Disease*, 1990, 323, 645-655.

Allen, A. D.; Hart, D. N.; Hechinger, M. K.; Slattery, M. J.; Chesson II, C. V.; Vidikan, P. "Leukocyte Adhesion Molecules as a Cofactor in AIDS: Basic Science and Pilot Study," *Medical Hypotheses*, 1995, 45, 164-168.

The Merck Manual, 16th Ed., (Berkow, R.; Fletcher, A. J.; Beers, M. H. eds., Merck Research Laboratories, 1992), 442-443.

"Zidovudine for the Prevention of HIV Transmission from Mother to Infant," *MMWR (Morbidity and Morality Weekly Report*, 1994, 43, 285-287.

Vermot-Desroches, C.; Rigal, D.; Bemaud, J. *Molec. Immunol.*, 1991, 28, 1104.

Van Waes, C.; Carey, T. E. "Overexpression of the A9 Antigen/α6β4 Integrin in Head and Neck Cancer," *Molecular Biology And Genetics*, 1992, 25, 1117-1139.

Carey, T. E.; Laurikainen, L.; Nair. T.; Reinke, T. S.; Coling, D. E.; Wolf, G. T.; Van Waes, C.; Liebert, M.; Marcelo, C. "Regulation of Expression and Phosphorylation of A9/$\alpha^6\beta 4$ Integrin in Normal and Neoplastic Keratinocytes," *Monogr. Natl. Cancer Inst.*, 1992, 75-86.

Pollard, H. B.; Pazoles, C. J.; Creutz, C. E.; Zinder, O. "Role of Intracellular Proteins in the Regulation of Calcium Action and Transmitter Release During Exocytosis," *Monogr. Neural Sci.*, 1980, 7, 106-116.

Mosby, "The Lung: Post-Traumatic Pulmonary Insufficiency," Multiple Organ Failure: Patient Care and Prevention (Chapter 10), 235-263 (1990).

Singh, U. P.; Chauhan, V. B. Wagner, K. G.; Kumar, A. "Effect of Ajoene, a Compound Derived from Garlic (allium sativum), on Phytophthora Drechsleri F. Sp. Cajani," *Myocolgia*, 1992, 84, 105-108.

Springer, T. A. "Adhesion Receptors of the Immune System," *Nature*, 1990, 346, 425-434.

Blobel, C. P.; Wolfsberg, T. G.; Turck, C. W.; Myles, D. G.; Primakoff, P.; White, J. M. "A Potential Fusion Peptide and an Integrin Ligand Domain in a Protein Active in Sperm-Egg Fusion," *Nature*, 1992, 356, 248-252.

Connor, E. M.; Sperling, R. S.; Gelber, R. Kiselev, P.; Scott, G.; O'Sullivan, M. J.; VanDyke, R.; Bey, M.; Shearer, W.; Jacobson, R. L.; Jimenez, E.; O'Neill, E.; Bazin, B.; Delfraissy, J-F.; Culnane, M.; Coombs, R.; Elkins, M.; Moye, J.; Stratton, P.; Balsley, J. "Reduction of Maternal-Infant Transmission of Human Immunodeficiency Virus Type 1 with Zidovudine Treatment," *The New England J. of Medicine*, 1994, 331, 1173-1180.

Hamilton, J. D.; Hartigen, P. M.; Simberkoff, M. S.; Day, P. L.; Diamond, G. R.; Dickenson, G. M. Drusano, G. L.; Egorin, M. J.; George, W. L.; Gordin, F. M.; Hawkes, C. A.; Jensen, P. C.; Klimas, N. G.; Labriola, A. M.; Lahart, C. J.; O'Brien, W. A.; Oster, C. N.; Weihold, K. J.; Wray, N. P.; Zolla-Pazner, S. B.; "A Controlled Trial of Early Versus Late Treatment with Zidovudine in Symptomatic Human Immunodeficiecy Virus Infection," *The New England Journal of Medicine*, 1992, 326, 437-443.

Talbott, G. A.; Sharar, S. R.; Harlan, J. M.; Winn, R. K. "Leukocyte-Endothelial Interactions and Organ Injury: The Role of Adhesion Molecules," *New Horizons*, 1994, 2, 545-554.

Neeper, M. P.; Jacobson, M. A. "Sequence of a cDNA Encoding the Platelet Aggregation Inhibitor Trigramin," *Nucleic Acids Research*, 1990, 18, 4255.

Clapham, P.; McKnight, A.; Simmons, G.; Weiss, R. "Is CD4 Sufficient for HIV Entry? Cell Surface Molecules Involved in HIV Infection," *Phil. Trans. R. Soc. Lond. B*, 1993, 342, 67-73.

Wagner, H.; Wierer, M.; Fessler, B. "Effects of Garlic Constituents on Arachidonate Metabolism," *Planta Med.*, 1987, 53, 305-306.

Weber, et al., "In Vitro Virucidal Effects of *Allium sativum* (Garlic) Extract and Compounds," *Planta Med.*, 1992, 58, 417-423.

Jansen et al., *Planta Medica*, 1987, 53, 559-62.

Bayer et al., *Planta Medica*, 1988, 54, 560 K1-6.
Knobloch et al., *Planta Medica*, 1988, 54, 561-62, K1-9.
Ziegler et al., *Planta Medica*, 1989, 55, 372-78.
Jansen et al., *Planta Medica*, 1989, 55, 434-49.
Jansen et al., *Planta Medica*, 1989, 440-45.
Iberl, B. et al., *Planta Medica*, 1990, 56, 202-11.
Iberl, B. et al., *Planta Medica*, 1990, 56, 320-26.
Lawson, L. D.; Wang, Z-Y. J.; Hughes, B. G. "Identification and HPLC Quantitation of the Sulfides and Dialk(en)yl Thiosulfinates in Commercial Garlic Product," *Planta Medica*, 1991, 57, 363-70.
Blania, G.; Spangenberg, B. "Formation of Allicin from Dried Garlic (*Allium sativum*): A Simple HPTLC Method for Simultaneous Determination of Allicin and Ajoene in Dried Garlic and Garlic Preparations," *Planta Medica*, 1991, 57, 371-75.
Tsai, Y.; Cole, L. L.; Davis, L. E.; Lockwood, S. J.; Simmons, V.; Wild, G. C. "Antiviral Properties of Garlic: *In Vitro* Effects on Influenza B., Herpes Simplex and Coxsackie Viruses," *Planta Medica*, 1985, 460-461.
Douvas, A.; Sobelman, S. "Multiple Overlapping Homologies Between Two Rheumatoid Antigens and Immunosuppressive Viruses," *Proc. Nat'l. Acad. Sci USA*, 1991, 88, 6328-6332.
Garsky et al., "Chemical Synthesis of Echistatin, a Potent Inhibitor of Platelet Aggregation from *Echis carinatus*: Synthesis and Biological Activity of Selected Analogs," *Proc. Nat'l Acad. Sci. USA*, 1989, 86, 4022-4026.
Chao, et al., "*Agkistrodon piscivorous piscivorus* Platelet Aggregation Inhibitor: A Potent Inhibitor of Platelet Activation", *Proc. Nat'l Acad. Sci. USA*, 1989, 86, 8050-8054.
Dennis et al., "Platelet Glycoprotein IIb-IIIa Protein Antagonists from Snake Venoms: Evidence for a Family of Platelet-Aggregation Inhibitors," *Proc. Nat'l Acad. Sci. USA*, 1990, 87, 2471-2475.
Johnson et al., *Proc. Natl. Acad. Sci. USA*, 1989, 86, 641-644.
Ferguson, T. A.; Mizutani, H.; Kupper, T. S. "Two Integrin-Binding Peptides Abrogate T Cell-Mediated Immune Responses *In Vivo*," *Proc. Natl. Acad. Sci. USA*, 1991, 88, 8072-8076.
Barillari et al. *Proc. Natl. Acad. Sci. USA*, 1993, 90, 7941-44.
Shalinsky et al., *Prostaglandins*, 1989, 37, 135-48.
Dennis et al., "Binding Interactions of Kistrin With Platelet Glycoprotein IIb-IIIa: Analysis by Site-Directed Mutagenesis," *Proteins: Structure, Function and Genetics*, 1993, 15, 312-321.
Kourounakis et al., *Research Communications in Chemical Pathology and Pharmacology*, 1991, 74, 249-52.
Hansen et al., *Scan J. Infect. Dis.*, 1991, 23, 31-36.
Hildreth et al., *Science*, 1989, 244, 1075-1078.
Arthur, L. O.; Bess Jr., J. W.; Sowder II, R. C.; Benveniste, R. E.; Mann, D. L.; Chermann, J-C.; Henderson, L. E. "Cellular Proteins Bound to Immunodeficiency Viruses: Implications for Pathogenesis and Vaccines," *Science*, 1992, 258, 1935-1938.
J.C., "What Causes The Immune System Collapse Seen In AIDS?", *Science*, 1993, 260, 1256.
Gougeon, M-L.; Montagnier, L. "Apoptosis in AIDS," *Science*, 1993, 260, 1269-1270.
Haynes, B. F. "Scientific and Social Issues of Human Immunodeficiency Virus Vaccine Development," *Science*, 1993, 260, 1279-1286.

Johnston, M. I.; Hoth, D. F. "Present Status and Future Prospects for HIV Therapies," *Science*, 1993, 260, 1286-1293.
Adler, M.; Lazarus, R. A.; Dennis, M. S.; Wagner, G. "Solution Structure of Kistrin, a Potent Platelet Aggregation Inhibitor and Gp IIb-IIIa Antagonist," *Science*, 1991, 253, 445-448.
Paul, W. E. "Reexamining AIDS Research Priorities," *Science*, 1995, 267, 633-636.
Li, C. J.; Friedman, D. J.; Wang, C.; Metelev, V.; Pardee, A. B. "Induction of Apoptosis in Uninfected Lymphocytes by HIV-1 Tat Protein," *Science*, 1995, 268, 429-431.
Samuelsson, B.; Dahlén, S-E.; Lindgren, J. A.; Rouzer, C. A.; Serhan, C. N. "Leukotrienes and Lipoxins: Structures, Biosynthesis, and Biological Effects," *Science*, 1987, 237, 1171-1176.
Inghirami, G.; Grignani, F.; Sternas, L.; Lombardi, L.; Knowles, D. M.; Dalla-Favera, R. "Down-Regulation of LFA-1 Adhesion Receptors of LFA-1 Adhesion Receptors by C-myc Oncogene in Human B Lymphoblastoid Cells," *Science*, 1990, 250, 682-686.
Block, E. "The Chemistry of Garlic & Onions," *Scientific American*, 1985, 252, 114-119, 128.
Ingber, D. E. "Extracellular Matrix as a Solid-State Regulator in Angiogenesis: Identification of New Targets for Anti-Cancer Therapy," *Seminars In Cancer Biology*, 1992, 3, 57-63.
Collman, R.; Nathanson, N. "Human Immuniodeficiency Virus Type-1 Infection of Macrophages," *Seminars in Virology*, 1992, 3, 185-202.
Gonzalez-Scarano, F.; Harouse, J. M.; Kenny, J. J.; Kunsch, C.; Spitalnik, S. L.; Wigdahl, B. "Human Immunodeficiency Virus Infection of Neural Cells," *Seminars in Virology*, 1992, 3, 225-234.
Vedder, N. B.; Fourty, B. W.; Winn, R. K.; Harlan, J. M.; Rice, C. L. "Role of Neutrophils in Generalized Reperfusion Injury Associated with Resuscitation from Shock," *Surgery*, 1989, 106, 509-16.
Mosby, "Theories and Common Threads in Multiple Organ Failure, Multiple Organ Failure," Patient Care and Prevention (Chapter 26), 473-486 (1990).
Shebuski, R. J.; Ramjit, D. R.; Sitko, G. R.; Lumma, P. K.; Garsky, V. M. "Prevention of Canine Coronary Artery Thrombosis with Echistatin, a Potent Inhibitor of Platelet Aggregation from the Venom of the Viper, *Echis carinatus*," *Thrombosis and Haemostasis*, 1990, 64, 576-581.
Cook, N. S.; Bruttger, O.; Pally, C.; Hagenbach, A. "The Effects of Two Synthetic Glycoprotein IIb/IIIa Antagonists, Ro 43-8857 and L-700,462, on Platelet Aggregation and Bleeding in Guinea-Pigs and Dogs: Evidence that Ro 43-8857 is Orally Active," *Thrombosis and Haemostasis*, 1993, 70, 838-847.
Apitz-Castro, R.; Cabrora, S.; Cruz, M. R.; Ledozma, E.; Jain, M. K. "Effects of Garlic Extract and of Three Pure Components Isolated From It on Human Platelet Aggregation, Arachidonate Metabolism, Release Reaction and Platelet Ultrastructure," *Thrombosis Research*, 1983, 32, 155-69.
Apitz-Castro et al., *Thrombosis Research*, 1986, 42, 303-11.
Mohammed et al., *Thrombosis Research*, 1986, 44, 793-806.
Lawson, L. D.; Ransom, D. K.; Hughes, B. G. "Inhibition of Whole Blood Platelet-Aggregation by Compounds in Garlic and Commercial Garlic Products," *Thrombosis Research*, 1992, 65, 141-56.
Spannagl, M.; Hoffmann, H.; Siebeck, M.; Weipert, J.; Schwarz, H. P.; Schramm, W. "A Purified Antithrombin III—Heparin Complex as a Potent Inhibitor of Thrombin in Porcine Endotoxin Shock," *Thrombosis Research*, 1991, 61, 1-10.

Omori-Satoh et al., "Purification and Characterization of Cytotoxic Factors in the Venom of the Okinawa Habu (*Trimeresurus flavoviridis*)," *Toxicon*, 1986, 24, 1045-1053.

Kin et al, "Effects of Snake Venom Proteins on Blood Platelets," *Toxicon*, 1990, 28, 1387-1422.

Kini et al., "Structural Domains in Venom Proteins: Evidence That Metalloproteinases and Nonenzymatic Platelet Aggregation Inhibitors (Disintegrins) From Snake Venoms are Derived by Proteolysis From A Common Precursor," *Toxicon*, 1992, 30, 265-293.

Rossen, R. D.; Smith, C. W.; Laughter, A. H.; Noonan, C. A.; Anderson, D. C.; McShan, W. M.; Hurvitz, M. Y.; Orson, F. M. "HIV-1-Stimulated Expression of CD11/CD18 Integrins and ICAM-1: A Possible Mechanism for Extravascular Dissemination of HIV-1-Infected Cells," *Trans. Ass. Am. Physicians*, 1989, 102, 117-130.

Yeston, N. S.; Palter, M. "The Lung In Shock," Treatment of Shock Principles and Practice, (Barrett, J.; Nyhus, L. M. eds., Lea & Febiger, Second Edition, 1986), Chapter 4, pp. 59-80.

Nemerow, G. R.; Gheresh, D. A.; Wickham, T. J. "Adenovirus Entry Into Host Cells: a Role for $\alpha_v$ Integrins," *Trends in Cell Biology*, 1994, 4, 52-55.

Isberg, R. R.; Van Nhieu, G. T. "Binding and Internalization of Microorganisms by Integrin Receptors," *Trends in Microbiology*, 1994, 2, 10-14.

Chammas, R.; Brentani, R. "Integrins and Metastases: An Overview," *Tumor Biol.*, 1991, 12, 309-320.

Dullege et al., 1992, VIII International Conference on AIDS, "Transplacental Transfer of ICD4-IgC Given One Week and Immediately Prior to Birth: Safety and Pharmacokinetics in HIV-1 Seropositive Pregnant Women and their New Born Infants," PoB 3028.

Tatarintsev, A.; Makarova, T.; Karamov, E.; Kornilaysva, G.; Vrzheshch, P.; Schegolev, A.; Yarshov, D.; Turgiev, A. "Ajoene Blocks HIV-Mediated Syncytia Formation: Possible Approach to 'Anti-Adhesion' Therapy of AIDS," VIII Int'l Conf. on Aids, Amsterdam, Conference abstract, Jul. 19-24, 1992.

Sato, H.; Orenstein, J.; Dimitrov, D.; Martin, M. "Cell-to-Cell Spread of HIV-1 Occurs within Minutes and May Not Involve the Participation of Virus Particles," *Virology*, 1992, 186, 712-724.

Faurc, E.; Yahi, N.; Zider, A.; Cavard, C.; Champion, S.; Fantini, J. "Physical Contact with Lymphocytes is Required for Reactivation of Dormant HIV-1 in Colonic Epithelial Cells: Involvement of the HTV-1 LTR," *Virus Research*, 1994, 34, 1-13.

Heicappell, R.; Ackermann, R. "Current Strategies for Immunotherapy of Renal Cell Carcinoma," *World Journal of Urology*, 1991, 9, 204-209.

Hirvonen, J.; Rintahaka, P.; Lapinlampi, T.; Huttunen, P. "Anaphylatic Death: The Effect of Aminoguanidine and Heparin on Histamine and Stress Hormones in Guine Pigs," *Z. Rechtsmed.*, 1989, 102, 297-304.

Koch, H. P. et al., Garlic the Science and Therapeutic Application of *Allium sativum* L. and Related Species, (Koch, P. H.; Lawson, L. D. eds. Williams & Wilkins 1997) p. 56.

* cited by examiner

CHIRAL INTEGRIN MODULATORS AND METHODS OF USE THEREOF

RELATED APPLICATIONS

This application is the National Stage of International Application No. PCT/US01/21826, filed Jul. 10, 2001, which claims the benefit of U.S. Provisional Application No. 60/217,651, filed Jul. 10, 2000.

BACKGROUND OF THE INVENTION

Integrins are heterodimeric transmembrane glycoproteins which, inter alia, act as cell receptors for various entities, herein termed collectively "integrin ligands," including, for example, surface molecules of other cells and extracellular matrix (ECM) proteins. Both soluble and immobilized integrin ligands are known to be ordinarily bound by integrins. Integrins are found on most types of cells. Ligand binding by integrins may result in or occur in association with a series of additional cellular events involving one or more cellular functions. These cellular events and functions, some of which are discussed below for illustrative purposes, are termed "integrin-mediated." For a general review of integrins, see, *Guidebook to the Extracellular Matrix and Adhesion Proteins* (Kreis, et al, Eds.), 1993, and Pigot, et al., *The Adhesion Molecule Facts Book*, Academic Press, 1993.

One such integrin-mediated cellular function is signaling. For instance, certain integrins are known to transfer information from the inside to the outside of the cell (inside-out signaling) or from the outside to the inside of the cell (outside-in signaling), although other types of signaling may also occur, as may combinations thereof. An example involving inside-out signaling is the process whereby an integrin acquires or expresses affinity for ligands in response to intracellular events (integrin upregulation). Binding of integrin ligands to certain integrins (e.g., in the case of integrin-mediated cell adhesion) may initiate signal transduction events, in a manner similar to that described for other cell surface receptors. Signals thus elicited are termed outside-in signals and are involved in the regulation of various cell responses, which may include gene expression, cell differentiation, and cell proliferation.

Signaling may result in the clustering of cellular molecules in localized areas of cellular membrane, e.g., in the association of integrins with each other (and other molecules) by lateral interactions. The formation of such clusters may influence various integrin functions in multiple ways, including, for example, by additional or secondary signaling events or interactions, and by altered ligand affinity.

The integrin-mediated function of adhesion is, or various integrin-mediated events associated with adhesion are, important for a variety of physiological and pathological responses. The extent of adhesion is functionally related to integrin signaling. For example, in association with initial integrin-dependent adhesion to a substratum, certain cells change their shape and start spreading on the surface of the stratum, using integrins for establishing new contacts with the underlying proteins (e.g., extracellular matrix (ECM) components). In motile cells, the whole array of integrin-mediated events involving adhesion—initial contact, cell shape change, cell spreading, and cell locomotion—is sometimes termed "the adhesion cascade" (Sharar, S. R., et al., The Adhesion Cascade and Anti-Adhesion Therapy: An Overview, 16 *Springer Semin. Immunopathol.* 359, 1995). Adhesion cascades are viewed as integral to one or more familiar cell motility patterns, including angiogenesis, lymphocyte homing, tumor cell metastasis, and cell migration processes associated with wound healing, although similar cascade mechanisms are also viewed as operative even in the absence of cell locomotion (e.g., in platelet adhesion and aggregation). Extravasation of neutrophils is described below in greater detail, as a paradigmatic integrin-mediated adhesion cascade (Hub, E., et al., Mechanism of Chemokine-Induced Leukocyte Adhesion and Emigration, *Chemoattractant Ligands and Their Receptors* (Horuk, R., Ed.), Boca Raton, CRC Press, 1996, 301).

The onset of extravasation is heralded by the appearance in the circulation of chemotactic factors, or chemoattractants (i.e., specific substances that initiate cell migration along their concentration gradients). Chemoattractants (e.g., chemokines, bacterial peptides, and products of complement activation) activate neutrophils to upregulate their integrin receptors (neutrophil integrins include, e.g., LFA-1 [CD11a/CD18], CR3 [also known as Mac-1, CD11b/CD18], and gp150,95 [CD11c/CD18]). Neutrophils thus activated adhere to endotheliocytes, change shape, and spread on the endothelial surface. Thereafter, the stimulated motile apparatus of the neutrophils gives rise to migration, and the neutrophils start moving, first across the endothelial layer and further, through the perivascular ECM, towards the source of the chemotactic stimulus, e.g., pathogenic bacteria invading a certain bodily tissue. During the whole process, from the initial firm contact with the endothelium to the cessation of locomotion at the destination site, various integrins serve to attach the neutrophil to the substrata it encounters, enabling its recruitment to the locus of infection.

Another integrin-mediated function is cell-cell fusion. Under physiological conditions, fusion is a developmentally regulated stage in the differentiation of certain multinucleate cells (e.g., osteoclasts, myocytes, and syncytiotrophoblasts), and fusion is also a prerequisite to fertilization (in the case of sperm-egg fusion). Fusion is effected by specialized cellular systems involving integrins (see, e.g., refs. cited in Huovila, A.-P. J., et al., ADAMs and Cell Fusion, 8 *Current Opin. Cell. Biol.* 692, 1996 and Ohgimoto, S., et al., Molecular Characterization of Fusion Regulatory Protein-1 [FRP-1] that Induces Multinucleate Giant Cell Formation of Monocytes and HIV gp160-Mediated Cell Fusion: FRP-1 and 4F2/CD98 Are Identical Molecules, 155 *J. Immune.* 3585, 1995).

The ability to undergo recirculation from intracellular compartments to the cell surface and vice versa is a common property of divers cellular receptors, including integrins (see, e.g., Handagama, P., et al., Kistrin, an Integrin Antagonist, Blocks Endocytosis of Fibrinogen into Guinea-Pig Megakaryocyte and Platelet alpha-Granules, 91 *J. Clin. Invest.* 193, 1993). This capability of integrins facilitates the mediation of other cellular functions by transporting into the cell extracellular material (e.g., soluble proteins, particulate matter, and other cells). Integrin-mediated internalization is used by certain microorganisms to invade their targets. For example, CR3 mediates entry of iC3b-opsonized HIV-1 and HIV-2 into CD4-negative lymphocytic and monocytic cells (Boyer, V., et al., Complement Mediates Human Immunodeficiency Virus Type 1 Infection of a Human T cell Line in a CD4- and Antibody-Independent Fashion, 173 *J. Exp. Med.* 1151, 1991).

The above-delineated functions of integrins are illustrative only, as other characterizations of integrin functions can also be made. Moreover, the integrin-mediated functions as delineated herein are overlapping and interrelated. In the case of neutrophil extravasation, for example, the initial chemotactic signal activating the cells is commonly functionally associated with in integrin upregulation (inside-out signaling) and adhesion to the endothelial surface. This adhesion event, in turn, is associated with outside-in signal, enabling the neutrophil to change its shape, which is a prerequisite to the spreading and migration of the cell. Likewise, when the neutrophil that has arrived to the source of chemoattractants establishes an adhesive interaction with the bacteria by means of integrins, an outside-in signal is transduced, which is associated with the initiation of internalization of the integrins involved, together with the bacteria attached thereto (phagocytosis).

Furthermore, regarding outside-in integrin signaling, certain cellular processes are co-mediated by several signaling systems acting in concert. In the case of neutrophils extravasating to the tissues to phagocytose bacteria, the neutrophils receive signals by means of the receptors of the chemoattractant (along the concentration gradient of which the movement occurs) and by means of distinct integrins (those that attach it to the substratum and, subsequently, those recognizing the bacteria). This interplay of signals mediates the antibacterial machinery of the neutrophils with the consequence that only upon contact with the bacteria, which is established by means of a particular type of integrin, are the constituents of the intracellular granules released and reactive oxygen species formed. As a result, the formation and release of microbicidal substances take place preferentially at sites of contact with bacteria, enabling effective killing of the bacteria and preventing the destruction of host tissue (Wright, S. D., Receptors for Complement and the Biology of Phagocytosis [Chapter 25], *Inflammation: Basic Principles and Clinical Correlates* [Gallin, J. I., et al., Eds.], 2nd Ed., New York, Raven Press, 477, 1992).

Clearly, a broad range of cellular activities can be regulated by modulating certain integrin functions with appropriate agents. One such integrin-modulating agent is ajoene (4,5,9-trithiadodeca-1,6,11-triene-9-oxide):

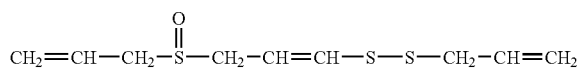

Ajoene, and a precursor thereof, can be isolated from products derived from extracts of garlic (*Allium sativum*). As the garlic is crushed, alliin in the garlic comes into contact with alliinase in the cell wall to form allicin. Then, in the presence of a polar solvent, allicin may form ajoene.

Ajoene has been previously shown to inhibit platelet aggregation by inactivating allosterically the platelet integrin, GP IIb/IIIa (Apitz-Castro, R., et al., 141 *Biophys. Res. Commun.* 145, 1986). It has been demonstrated that stereoisomers of ajoene (ie., E- and Z-4,5,9-trithiadodeca-1,6,1-triene-9-oxides) exhibit no significant differences in their effects on platelets (Block, E., et al., 108 *J. Am. Chem. Soc.* 7045, 1986). For this reason, most of subsequent studies of the integrin modulation by ajoene were carried out on various mixtures of the E- and Z-isomers. It was shown, for example, that ajoene is a potent inhibitor of a wide variety of adhesion-dependent processes, including neutrophil aggregation, HIV transmission (Tatarintsev, A. V., et al., 6 *AIDS* 1215, 1992), and tumor metastasis. U.S. Patents issued to Tatarintsev, et al. disclose the use of ajoene for treatment of inflammation (U.S. Pat. No. 5,948,821), arthritis (U.S. Pat. No. 5,856,363), and tumors (U.S. Pat. No. 5,932,621), as well as for contraception (U.S. Pat. No. 5,863,954) and inhibition of immune responses (U.S. Pat. No. 5,863,955).

All of these diseases and conditions involve integrin-mediated processes. See also PCT application WO 97/25031, which describes the use of ajoene to treat additional diseases and conditions which involve integrin-mediated processes.

The presence of the sulfoxide group in the molecule of ajoene (a prerequisite to optical isomerism) and stereoisomerism of the compound (around the double bond at carbon 6) create a possibility for four optical isomers (enantiomers): E(R)-, E(S)-, Z(R)-, and Z(S)-4,5,9-trithiadodeca-1,6,11-triene-9-oxides. This possibility has never been suggested in the art. Moreover, in the case of allicin (which also contains a sulfoxide radical), even the existence of optical activity has been questioned, so that the existence of enantiomers, let alone stable enantiomers, would have been considered unlikely (*Garlic: The Science and Therapeutic Application of Allium Sativum L. and Related Species*, page 56 (Lawson L. D., et al., Eds., 1997)).

OBJECTS OF THE INVENTION

An object of the present invention is to provide enantiomers of ajoene.

Another object of the present invention is to characterize the integrin-modulating activity of the enantiomers, with a view to identifying species that would differ in activity from racemic mixtures. The word "racemic" is used herein in its strict sense to designate a chemical compound that contains equal quantities of dextrorotatory and levorotatory enantiomers and, therefore, does not rotate the plane of incident polarized light (*The American Heritage Dictionary of the English Language*, 1996).

Yet another object of the present invention is to provide methods of preparing ajoene enantiomers.

A final object of the present invention is to provide stereoselective, chiral integrin modulators and methods of use thereof.

SUMMARY OF THE INVENTION

The objects of the invention have been attained. The invention provides enantiomers of ajoene: E(+)-, E(−)-, Z(+),- and Z(−)-4,5,9-trithiadodeca-1,6,11-triene-9-oxides. The invention further provides methods of preparing the enantiomers. The invention also provides approaches to, and methods of, assessment of the integrin-modulating activity of the enantiomers. The invention further provides stereoselective, chiral integrin modulators (CIMs), as further defined and specified herein. Specifically, such modulators include derivatives of Z(−)-4,5,9-trithiadodeca-1,6,11-triene-9-oxide of the formula:

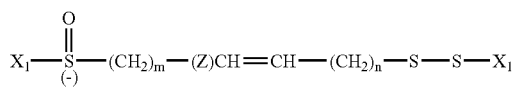

wherein:

each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, anunonio, nitrozo, nitro, mercapto, or sulfo;

R is hydrogen, lower alkyl, aryl, or an aryl substituted with one or more lower alkyls;

m is 0–30; and n is 0–30.

The prototypal CIM of this invention is Z(−)-4,5,9-trithiadodeca-1,6,11-triene-9-oxide.

The invention also provides methods of using the above CIMs. First, the invention provides a method of modulating an integrin-mediated function of one or more cells using the CIMs. Second, the invention provides methods for the treatment of a variety of disorders, diseases and conditions. In particular, the invention provides: (1) methods of treating or preventing a disorder, disease or condition in which one or more integrins play a role; (2) methods of treating or preventing thrombotic disorders and diseases/conditions arising therefrom (embolism, ischemia, infarction, etc.); (3) methods of treating or preventing inflammation and inflammatory diseases; (4) methods of treating, preventing, or inhibiting the transmission of viral infections; (5) methods of treating shock; (6) a method of treating arthritis; (7) methods of contraception; (8) methods of treating or suppressing adverse, undesirable or self-destructive immune responses, including acute and chronic hypersensitivity reactions (such as anaphylaxis and allergy), transplant rejection, and graft-versus-host disease (GVHD); (9) methods of treating autoimmune diseases; (10) methods of inhibiting undesirable integrin-mediated cell-cell fusion; (11) methods of inhibiting the formation of lesions; (12) methods of treating psoriasis; (13) methods of treating atherosclerosis; (14) methods of treating diseases or conditions involving a plurality of integrin-dependent etiopathogenetic mechanisms; (15) methods of inhibiting the transfer of genetic material; and (16) methods of treating cancer, preventing metastasis of tumors, or inhibiting certain (integrin-mediated) types of carcinogenesis.

The invention further provides pharmaceutical compositions. The compositions comprise the above CIMs and a pharmaceutically-acceptable carrier.

In addition, the invention provides a method of treating a tissue by contacting the tissue with a CIM. Such treatment improves the condition of the tissue for subsequent use, as compared to tissue which is not treated with a CIM. In particular, tissue which is to be transplanted into a recipient may be treated with a CIM prior to, in the course of, and/or after harvesting, and the chances of the tissue being successfully transplanted will be increased.

Finally, the invention provides a kit for treating tissue. The kit comprises a container holding one or more of the above CIMs.

Figure 1:
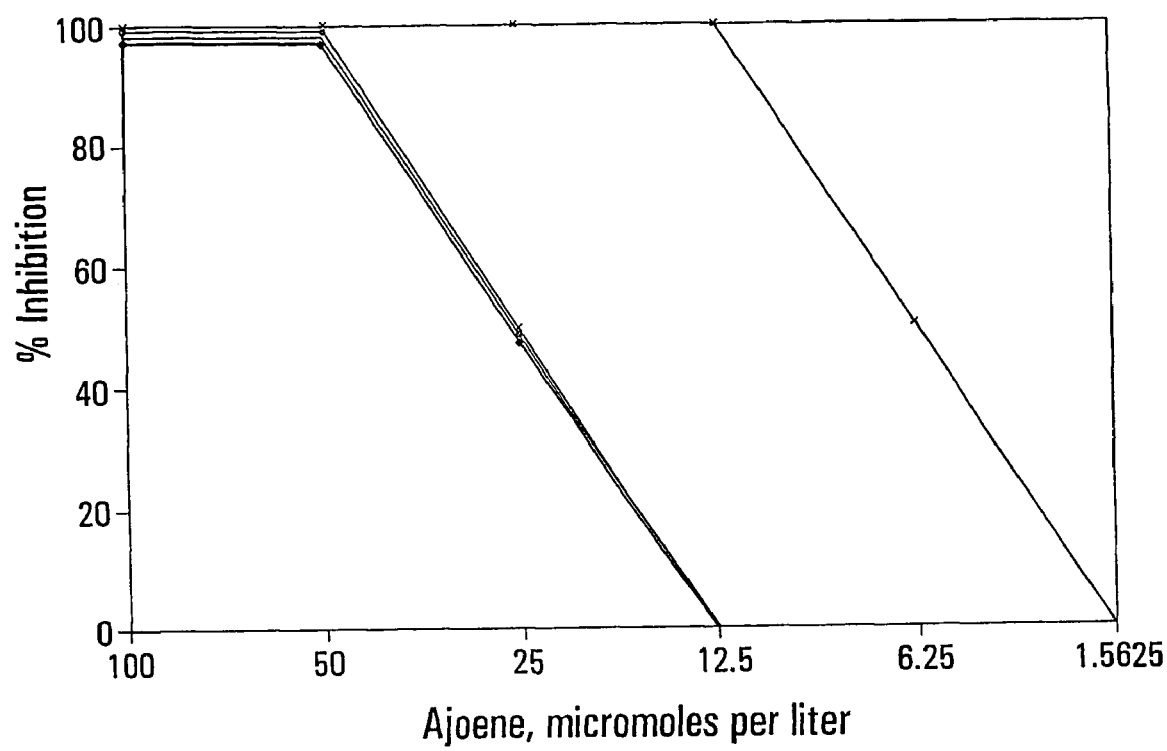
FIG. 1 is a graph of HIV-induced syncytium formation as a percentage of untreated control versus concentration (micromoles per liter) of the unseparated 3:1 mixture of racemic Z- and E-ajoenes (♦), Z(+)-ajoene (+), racemic E(−)ajoenes (○), and Z(−)-ajoene (X) (curves 1 through 4, left to right, respectively).

For all the curves, the effect of ajoene enantiomers and enantiomer mixtures on the fusion of cultured, intact H9 cells with HIV-$1_{RF}$-infected H9 cells is disclosed. The vertical graph axis expresses the maximum amount of syncytia formed in the absence of the compounds (100 percent), while the points on the curves represent percentages of such an amount of syncytia formed in the presence of varying concentrations of the compounds and compound mixtures (micromoles per liter).

The coincidence of curves 1 through 3 and the leftward shift of curve 4 demonstrate that Z(−)-ajoene is at least four times more active than its Z(+) counterpart, racemic E-ajoene, or the unseparated 3:1 mixture of racemic Z- and E-ajoenes (the respective values of $IC_{100}$ are 12.5 and 50 micromoles per liter).

DETAILED DESCRIPTION OF THE PRESENTLY PREFERRED EMBODIMENTS

This invention provides enantiomers of ajoene: E(+)-, E(−)-, Z(+),- and Z(−)-4,5,9-trithiadodeca-1,6,11-triene-9-oxides. Bythis invention, ajoene maybe separated into the two pairs of enantiomers. Specifically, both (E) and (Z) racemic forms may be used as a starting material for the separation, although various (E)/(Z) mixtures may also be used. In one preferred embodiment, the enantiomers are structurally identified by at least two characteristics, including mobility in one or more organic solvent mixtures and optical activity, both detected at the same fixed temperature. Correspondingly, the enantiomers are designated E(+)-, E(−)-, Z(+),- and Z(−)-4,5,9-trithiadodeca-1,6,11-triene-9-oxides.

In addition, the invention discloses methods whereby the integrin-modulating activity of ajoene enantiomers may be assessed. One such method involves VLA-4-mediated adhesion of enzyme-labeled PM1 cells to VCAM-1-coated artificial substrata. Specifically, the cells were exposed to isolated ajoene enantiomers (or the vehicle thereof) and allowed to adhere to immobilized VCAM-1. Thereafter, the adherent cells were lyzed and, following addition of the substrate of the enzyme and incubation, the activity of the enzyme was measured spectrophotometrically. The value of this parameter, characterizing the number of the adherent cells, is inversely proportional to the integrin-modulating activity of the compound.

Another such method is based on the inhibition of HIV-mediated syncytium formation, a phenomenon known to depend on the functional activity of integrins. The purified Z enantiomers, racemic E-ajoene, and the original 3:1 mixture of racemic Z- and E-ajoenes were taken up in DMSO at a concentration of 10 mg/mL. Dilutions were made in RPMI 1640 medium containing 10% fetal calf serum and 10 MM HEPES (cRPMI). HIV-$1_{RF}$-infected H9 cells and uninfected H9 cells were washed with cRPMI and resuspended in cRPMI at a density of $4 \times 10^6$ per mL. Uninfected cells (50 µL) were mixed with serial dilutions of the compounds (100 µL) and incubated at 37° C. for 30 minutes before adding and mixing 50 µL of infected H9 cells. The plates were incubated at 37° C. for 6 to 15 hours before scoring syncytium formation.

By these methods, Z(−)-4,5,9-trithiadodeca-1,6,11-triene-9-oxide was at least four times more active as an integrin modulator than other enantiomers, racemic E-ajoene, or the unseparated 3:1 mixture of racemic E and Z-ajoenes. The unexpected superior activity of one out of the four enantiomers correlates with the presence in the molecule of the following trithia oxide structure:

$$\underset{(-)}{\overset{O}{\overset{\|}{-S}}}-CH_2-(Z)CH=CH-S-S- \quad (1)$$

It is, therefore, understood that chiral compounds containing the above core structure comprise a class of potent integrin modulators.

Specifically, the class of chiral integrin modulators (CIMs) includes compounds of the formula:

$$X_1-\underset{(-)}{\overset{O}{\overset{\|}{S}}}-(CH_2)_m-(Z)CH=CH-(CH_2)_n-S-S-X_1 \quad 2$$

wherein:
each $X_1$ may be the same or different than the other $X_1$ and each $X_1$ is hydrogen, an alkyl, an alkenyl, an alkynyl, an aryl, an aryl substituted with one or more $-NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

"Alkyl" means a straight-chain or branched-chain alkyl containing 1–10 carbon atoms or a cyclic alkyl containing 3–7 carbon atoms. "Lower alkyl" means a straight-chain or branched-chain alkyl containing 1–4 carbon atoms. Both terms include all isomers. Preferably, the alkyl is methyl, ethyl, propyl, iso-propyl, n-butyl, iso-butyl, sec-butyl, tert-butyl, pentyl, iso-pentyl, neo-pentyl, n-hexyl, or cyclohexyl.

"Alkenyl" means a straight-chain or branched-chain alkenyl containing 2–10 carbon atoms and at least one double bond. The term includes all isomers. Preferably, the alkenyl is vinyl, propenyl, or iso-propenyl.

"Alkynyl" means means a straight-chain or branched-chain alkynyl containing 2–10 carbon atoms and at least one triple bond. The term includes all isomers. Preferably, the alkynyl is ethynyl, 1-propynyl, or 2-propynyl.

"Aryl" means a group containing at least one aromatic ring. Preferably, the aryl is phenyl. The aryl may be substituted with one or more $-NO_2$ groups, in which case it is preferably m-nitrophenyl, p-nitrophenyl, o-nitrophenyl, 3,5-dinitrophenyl, or 2,4-dinitrophenyl. The aryl may also be substituted with one or more lower alkyls, in which case the point of attachment to the sulfur atoms in formula (2) or to an atom of one of the substituent groups listed above (e.g., RO—, RCO—, etc.) can be by means of an alkyl group or a ring carbon. Preferred aryls substituted with one or more lower alkyls are benzyl, o-tolyl, p-tolyl, m-tolyl, 3,5-xylyl, and 2,6-xylyl.

"Halogen" means fluoro, chloro, bromo, or iodo.
Preferred groups of the formula RO— are hydroxy, methoxy, ethoxy, phenoxy and benzyloxy.
Preferred groups of the formula RCO— are acetyl, formyl, and benzoyl.
Preferred groups of the formula RCOO— are formlyoxy or acetoxy.
Preferred groups of the formula ROCO— are methoxycarbonyl, ethoxycarbonyl, tert-butoxycarbonyl, and benzyloxycarbonyl.
Preferred groups of the formula $(R)_2N$— are amino, methylamino, ethylamino, phenylamino, dimethylamino, and diethylamino.
Preferred groups of the formula RCON— are acetylamino and benzoylamino.
A preferred group of the formula RN=N— is phenylazo.
A preferred group of the formula RS— is ethylthio.
A preferred group of the formula $RSO_2$— is methylsulfonyl.
A preferred group of the formula RSO— is methylsulfinyl.
A preferred group of the formula $RSO_2O$— is methylsulfonyloxy.
A preferred group of the formula RSOO— is methylsulfinyloxy.

One particularly preferred CIM of this invention is the prototypal compound, Z(−)-4,5,9-trithiadodeca-1,6,11-triene-9-oxide, that is, a compound of formula (2), wherein $X_1=X_1$=allyl, n=1, and n=0.

Isomeric mixtures of the compounds of formula (2) can be synthesized by methods well known in the art. See, e.g., U.S. Pat. Nos. 4,643,994 and 4,665,088, Block et al., *J. Am Chem. Soc.*, 108, 7045–7055 (1986) and Sendl et al., *Planta Med.*, 57, 361–362 (1991), the complete disclosures of which are incorporated herein by reference. The isomeric mixtures can then be separated as described below to obtain a desired CIM, such as Z(−)-4,5,9-trithiadodeca-1,6,11-triene-9-oxide.

In particular, U.S. Pat. No. 4,665,088 describes the synthesis of (E,Z)-4,5,9-trithiadodeca-1,6,11-triene-9-oxide. Briefly, garlic is subjected to any convenient extraction procedure which acts to isolate the allyl disulfide oxide component of garlic so that this component can be thereafter dissolved in an appropriate lower alkanol for a time and at a temperature sufficient to form (E,Z)-4,5,9-trithiadodeca-1, 6,11-triene-9-oxide. To obtain higher yields, the garlic should be freshly cut, chopped or ground. Whole garlic cloves reduce yield, but can be satisfactorily used. The garlic pieces are blended with a volatile, water-miscible organic solvent such as a lower alkanol, ether, or acetone and are allowed to sit for several hours or days. The particulate material is usually removed prior to further processing. Vacuum concentration of the liquid and extraction of the aqueous residue with an appropriate solvent, such as diethyl ether, appears to increase the yield significantly. The extracted aqueous residue can be washed several times with water, dried and evaporated to increase the purity of the oil allyl disulfide oxide residue. The oily residue product is then dissolved in a volatile organic solvent, such as acetone or a lower alkanol in mixture with water (10–90%), and maintained at a temperature of from about −40° C. to a temperature less than about the reflux temperature of the organic solvent in mixture with the water. Generally, the higher the temperature, the lower the amount of time the mixture must be maintained at that temperature. It is generally desirable to adjust temperature to achieve a maintenance time of several hours, usually from about 10–72 hours. (E,Z)-4,5,9-trithiadodeca-1,6,11-triene-9-oxide can also be prepared as described in the next paragraph.

U.S. Pat. No. 4,643,994 describes the synthesis of isomeric mixtures of several compounds coming within the scope of formula (2) and describes a general synthetic scheme that can be used for preparing isomeric mixtures of compounds of formula (2). Briefly, an appropriate disulfide having the formula:

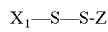 (3)

wherein Z is —(CH$_2$)$_m$—CH=CH—(CH$_2$)$_n$—, and m, n and X$_1$ are defined above, is treated with an oxidizing agent, preferably in the presence of a solvent, and preferably at a temperature of from about −40° C. to about 65° C. to produce a thiosulfinate of the formula:

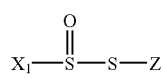 (4)

The thiosulfinate is then heated, typically refluxed, in the presence of an appropriate solvent, preferably a 60:40 organic solvent:water mixture to form a trithio oxide of the formula:

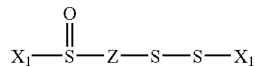 (5)

Typically, the reaction which causes the formation of the trithio oxide of formula (5) also causes the formation of minor products wherein each X$_1$ or Z can be Z or X$_1$, respectively. If a mixture of disulfides or thiosulfinates are used as starting compounds, the product will be a further mixture of products. The mixture of products can be separated at this point in the process by various means, such as extraction, or the mixture can be maintained as such through the next step(s). The compound (5) can be used directly to make CIM's of the invention or can be further oxidized to produce additional compounds of formula (2). Treatment with a stoichiometric (or slight excess) amount of oxidizing agent forms compounds of formula:

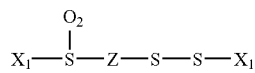 (6)

Treatment with further oxidizing agents at −30° C. to 40° C. produces compounds of formula:

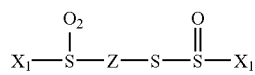 (7)

Continued treatment with an oxidizing agent produces compounds of formula:

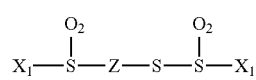 (8)

Each of compounds (7) and (8) can be reacted with a thiol of the formula X$_1$SH, or an alkali metal salt thereof, wherein X$_1$ is defined above, to produce further compounds having different selected substitutents as the X$_1$ moiety. These compounds can be purified by various means, including extraction, and used to make CIMs.

The CIMs can be purified from an isomeric mixture by high performance liquid chromatography (HPLC) on columns packed with sorbents that are capable of separating individual enatiomers from mixtures thereof. See the Examples below.

By this invention, safe and effective doses of the CIMs may inhibit the progression of an HIV infection in a patient or the infection of an uninfected patient by HIV. Specifically, Z(−)-ajoene is such an inhibitor, although other CIMs may also be used.

One of the characteristics the inhibition of HIV infection is the diminution of the formation of HIV-induced syncytia, in which HUV target cells, such as lymphocytes and monocytes, fuse together to form giant, multinucleate cells in HIV-infected patients. Transfer of genetic material between cells will, thereby, also be inhibited by CIMs, which inhibit fusion with cell membranes.

Additionally, because CIMs modulate pertinent integrin activity, it appears that CIMs inhibit the entry of the infective HIV material into its target cells, including CD4-negative cells, both virus-to-cell and cell-to-cell entry, and the production of HIV and other viruses by the infected cells. For these purposes, CIMs are preferably administered in a sufficient dose to provide a concentration approaching or exceeding 5 micromoles per liter of patient's blood plasma, although lesser concentrations may also be effective. This dose is effective when the CIMs are used alone or in a bi- or multi-therapy addressing different disease parameters (e.g., the function of viral enzymes).

In addition to infections caused by HIV and other viruses of the Retroviridae family, CIMs can be used locally or systemically to inhibit or prevent the transmission, in vivo and in vitro, of other viruses infecting humans and other animals. In particular, CIMs can be used to treat or prevent infections caused by viruses, the transmission of which involves fusion of at least a part of the virus with the membrane of the target cell that is to be infected. Such viruses include all enveloped viruses and other viruses that infect cells in this manner. The enveloped viruses include the Retroviridae, Herpesviridae (e.g., herpes simplex, HSV-2, varicella zoster, Epstein-Barr virus, and cytomegaly virus), Hepadnaviridae (e.g., hepatitis B), Flaviviridae (e.g., yellow fever virus and hepatitis C virus), Togaviridae (e.g. rubivirus, such as rubella virus, and alphavirus), Orthomyxoviridae (e.g., influenza virus), Paramyxoviridae (e.g., measles, parainfluenza, mumps and canine distemper viruses), Poxviridae (e.g., variola virus and vaccinia virus), and Rhabdoviridae (e.g., rabies virus). Other viruses that infect cells by fusing with the membrane include Papovaviridae (e.g., papillomavirus), Picornaviridae (e.g., hepatitis A virus and poliomyelitis virus), Rotaviridae, and Adenoviridae. In addition to inhibiting or preventing virus-to-cell entry, CIMs can also inhibit or prevent cell-to-cell transmission of viruses (e.g., by inhibiting or preventing syncytia formation or by inhibiting or preventing intercellular viral transfer between cells in contact or close proximity) and the production of viruses by infected cells.

CIMs also serve as agents that inhibit the adhesion, migration (e.g., chemotaxis or other infiltration of the tissue), and aggregation of various cell types and lines, including blood platelets and neutrophils. CIMs, therefore, exhibit benefit as agents for the treatment of pathologies derived from adhesion, migration, and aggregation of these and other cells, including thrombosis and various types of inflammation.

Thrombosis is defined as blockage of blood vessel(s) by thrombi, i.e., clots formed from fibrin and platelet aggregates, deposited on the inner surface of the vessel. Thrombi form in arteries (e.g., damaged as a result of a disease) or in veins (e.g., due to lengthy immobilization). If a thrombus or a blood clot is dislodged and moves through the bloodstream to create an obstruction outside the place of its formation, it becomes an embolus (hence the terms "thromboembolism" and "thromboembolic disease"). Thrombosis or thromboembolism of coronary arteries can cause heart attacks and myocardial infarction; the same processes in brain arteries cause stroke. Inhibition of platelet aggregation by CIMs would, therefore, arrest thrombosis at early stages, precluding the development of thrombotic and thromboembollic diseases.

Inflammation, a pathological process inherent in a variety of distinct diseases and illnesses, is defensive in nature, but potentially dangerous if uncontrolled. When viewed at the "whole body" level, an inflammation is most frequently characterized by several localized manifestations (indices), including hemodynamic disorders (e.g., hyperemia and edema), pain, temperature increment, and functional lesion. These inflammatory phenomena are underlain by events at the cellular and molecular levels. At the cellular level, inflammation is characterized by leukocyte extravasation (a process involving adhesion of leukocytes to the endothelium of the vessel wall and migration into tissue where they may phagocytose bacteria, viruses, and cell debris) and platelet aggregation (a mechanism, inter alia, whereby the spread of the infection is prevented). At the molecular level, inflammation is characterized by activation of at least three plasma defense systems (complement, kinin, and coagulation/fibrinolysis cascades) and by synthesis of cytokines and eicosanoids. When inflammation becomes generalized (as in the case of shock, for example), various indices of inflammation occur systemically throughout the entire organ/organism.

In cases of shock, platelets and leukocytes (principally neutrophils) aggregate in the blood vessels, leading to the development of a clinical condition known as multiple organ failure. The primary organ affected in shock patients is commonly the lung. Lung failure, or adult respiratory distress syndrome (ARDS), a destructive inflammation resulting from adhesion, aggregation, and degranulation of activated neutrophils in the pulmonary microvasculature, may be the main cause of death in patients suffering shock. CIMs may thus counteract at least part of the effects of shock, whether arising, for example, from sepsis, anaphylaxis, blood loss, or from other precipitating events.

CIMs can also be administered in effective dosages to suppress many other acute inflammatory processes, such as those associated with peritonitis, meningitis, and ischemia-reperfusion. Ischemia-reperfusion injury occurs (e.g., in heart, brain, kidney, liver, lung, intestinal tract, or any limb) when blood supply is abruptly stopped (ischemia) and then resumed (reperfusion) after a short period.

With the onset of ischeinia and the decrease in the perfusion pressure, neutrophils are retained in the capillaries. As the ischemia progresses, cytokines (and other chemoattractants) are released into the capillary lumina in regions of the tissue where the blood flow blockage has occurred, increasing the adhesiveness of the retained neutrophils to the endothelium and to each other. Aggregates of neutrophils thus formed obstruct postcapillary venules ("no-reflow," or "no-washout") and attenuate the restoration of the blood flow in the affected region, precluding its reoxygenation and extending the area of ischemia. Activated neutrophils trapped in the capillaries also release hydrolytic enzymes and reactive oxygen species (i.e., the armamentarium ordinarily used to defend the host against microorganisms), producing a destructive inflammation.

Restoration of the blood flow, however, further augments the severity of the inflammation thus developed. Neutrophils arriving to the previously ischemic region are activated (by chemoattractants and/or products released by the trapped neutrophils) and recruited into the tissue, where the defensive machinery of the cells is once again used against the host (secondary injury). Ischemia-reperfusion injury can also be generalized, e.g., in the case of resuscitation after hemorrhagic shock (Mazzone, A., et al., Leukocyte CD11/CD18 Integrins: Biological and Clinical Relevance, 80 *Haematologica* 161, 1995; see also, Reinhart W. H., Hemorheology: Blood Flow Hematology, 125 *Schweiz. Med. Wochenschr.* 387, 1995).

CIMs are also potent inhibitors of adhesive interactions for other cells, such as lymphoid cells. Adhesion of lymphocytes to each other and nonlymphoid cells is prerequisite to the development of any immune response. CIMs may, therefore, serve as agents for the prevention, treatment, and control of adverse, undesirable, and self-destructive immune responses.

One group of such immunopathologies comprises diseases stemming from divers allergic reactions (e.g., delayed type hypersensitivity, Arthus reaction, and anaphylaxis). Allergy is an anomalous immune response to antigen challenge, characterized by recruitment of specific leukocyte subsets (e.g., cytotoxic lymphocytes and/or eosinophils) to the tissue, resulting in inflammation. Development of allergic inflammation is the main component in the pathogenesis of many diseases and illnesses, including, e.g., asthma, eczema, *purpura pigmentosa chronica*, various vasculitides, and hay fever, in addition to those mentioned above. CIMs serve to control these diseases and illnesses.

Allograft rejection is another example of an undesirable immune response, in which the transplanted organ is recognized by the immune system as a foreign body ("non-self") and attacked in sequence by cytotoxic lymphocytes and phagocytes recruited from the circulation. This inflammatory response results in progressive disruption of the tissue, including graft necrosis. CIMs may be used to prevent cell recruitment into transplanted tissue and thereby prolong graft survival by reducing both acute and chronic aspects of rejection.

Moreover, the transplanted organ also contains lymphocytes, which, in turn, recognize their new environment as "non-self." The immune response initiated by these donor lymphocytes in the body of the recipient produces a condition known as graft-versus-host disease (GVHD), which can lead to injury, both acute and chronic. CIMs can contribute to the control of both acute and chronic GVHD.

Any method of treatment that suppresses both rejection and susceptibility to viruses (which, like cytomegaly virus, frequently contaminate the transplanted organs and decrease the probability of their engraftment) will have an extra benefit to the graft recipient. As discussed above, CIMs of instant invention exert pronounced antiviral effects, in addition to being potent anti-inflammatory agents. Thus, administration of CIMs to patients undergoing organ transplantation offers niuch promise as a novel therapeutic approach to the prevention of rejection.

Self-destructive responses are caused by the failure of the immune system to distinguish "self" from "non-self." This group of immunopathologies comprises a wide variety of diseases (herein termed collectively "autoimmune diseases"), including, without limitation, rheumatoid arthritis, systemic lupus erythematosus, Sjögren's syndrome, multiple sclerosis, insulin-dependent diabetes mellitus, glomerulonephritis, Graves disease, Hashirnoto's thyroiditis, and vasculitides. Other conditions and diseases may also fall into this category (see, e.g., the discussion of psoriasis below) or comprise a component that does so (chronic viral diseases stimulating an autoimmune response). In spite of pronounced differences in the clinical picture of the various autoimmune diseases, the underlying mechanisms involve, in every case, undesirable recruitment of leukocytes to organs/tissues affected, resulting in destructive inflammation. CIMs can be used to reduce or prevent this cellular recruitment and thereby suppress the abnormal immune response. Accordingly, CIMs may be used to treat autoimmune diseases.

The beneficial effects of CIMs are achieved because these substances are modulating the activity of integrins. As used herein, "modulate" means to affect the development or expression of modalities normally characterizing the ability of a particular integrin to perform any of its functions. A modulating agent may act on an integrin directly, e.g., by binding to or interacting with a portion of at least one subunit (alpha or beta) of the integrin. The agent may also act in some other fashion that is not considered direct, e.g., through any of the various cellular substances and structures which ordinarily interact with or enable the participation of specific integrins, alone, or in combination. These substances and structures include, without limitation, transmembrane proteins (e.g., integrins themselves and integrin-associated proteins), membrane phospholipids, intracellular molecules with messenger-like function (e.g., integrin-modulating factor), enzymes, and regulatory and signaling proteins. Thus, for example, a modulation may result from alteration in integrin conformation, disassociation of the alpha and beta integrin subunits (or any of the parts thereof), disassociation of integrin clusters (and of clusters formed by integrins with other proteins), or from the loss or variations of integrin-cytoskeleton connections, although modulation may also occur from other types of effects. The functions of integrins, as defined herein, are interrelated and include, inter alia, signaling, adhesion, fusion, and internalization.

As a result of its ability to modulate activities in which integrins participate, CIMs can be used to treat a plurality of diseases or conditions that involve undesirable integrin-mediated functions as a mechanism, including those described above. For instance, CIMs can be used to inhibit virus-cell fusion. Moreover, CIMs may be used to inhibit undesired cell-cell fusion.

Undesired cell-cell fusion can include, for example, cell-cell fusion (transitory or permanent) that results in the transfer of viral genetic material; cell-cell fusion that results in the formation of multinucleate cells (e.g., syncytia, giant cells, and osteoclasts); undesired fertilization of eggs by sperm; and the formation of multinucleate germinal cells (syncytiotrophoblast).

Thus, CIMs can be used as a contraceptive, being administered per vaginam (topically), per os, or in any other appropriate way, when used for this purpose. CIMs can prevent conception, however, at the stage of embryo implantation. For example, CIMs can prevent the initial adhesion of the blastocyst to the endometrium and the migration of cytotrophoblasts through the maternal epithelium (i.e., processes similar to certain steps in the leukocyte extravasation cascade and tumor cell metastasis).

Furthermore, CIMs are capable of inhibiting cytotrophoblast invasion, a process differing from extravasation in that it goes from the tissues to the vascular lumen and that the invading cells cross the blood-tissue barrier from outside of the vessel. For example, the production of proteolytic enzymes that are used by cytotrophoblasts to penetrate the basement membrane is governed by integrin outside-in signaling. Modulation of the signaling function of integrins by CIMs can either completely prevent the production of the requisite enzymes or attenuate it to an extent precluding invasion. A related mechanism underlies the ability of CIMs to block angiogenesis, preventing the blood supply to the fetal tissue. Thus, CIMs can be used as effective emergency contraceptives to prevent unwanted pregnancy or interrupt it at an early stage.

There are yet other mechanisms whereby CIMs, when desired, can exert contraceptive effects. For example, they can prevent the chemotactic response of sperm in the vaginal environment (a specific case of cell homing) and sperm interactions with the epithelium of the female genital tract. Moreover, CIMs can be administered to males to modulate integrins in sperm precursors and other testicular or epididymal cells, thereby interfering with the maturation processes and resulting in the production of fertilization-incompetent gametes or inhibition of fertilization-competent gametes.

The development of major bone diseases, including osteoporosis, is underlain by excessive bone resorption. This fundamental function is performed by osteoclasts. Osteoclasts are unique multinucleate bone cells formed by fusion of mononuclear progenitors called preosteoclasts. The regulation of osteoclast formation may be achieved by agents acting at various levels of osteoclast formation, including preosteoclast fusion (Zaidi, et al., Cellular Biology of Bone Resorption, 68 *Biol. Rev.* 197, 1993). CIMs can regulate bone resorption because it can inhibit the fusion of preosteoclasts necessary for the formation of osteoclasts.

Granulomas are characteristic of chronic inflammatory lesions, such as those found in tuberculosis and other chronic infections. Granulomas are also present in sarcoidosis, a chronic, systemic inflammatory disease of undescribed etiology. Granulomas present in cases of chronic infection and in sarcoidosis contain a large number of multinucleate giant cells formed by the fusion of macrophages. Other diseases associated with the formation of multinucleate cells include, without limitation, Crohn's disease, Langerhans cell histiocytosis, and giant cell arteritis. CIMs can be used to inhibit the formation of these giant multinucleate cells with beneficial therapeutic effects.

Excessive formation of fibrous interstitial tissue (i.e., fibrosis, or sclerosis) is characteristic of certain diseases (such as scleroderma and idiopathic pulmonaryfibrosis) and an outcome of chronic inflammatory processes (e.g., glomerular fibrosis). The development of fibrotic lesions and progression of fibrosis, associated with these conditions, diseases, and illnesses, has been linked to abnormal integrin expression and altered cell adhesion patterns. CIMs can, therefore, be used for treatment of fibrotic lesions, including the formation of keloid (scar tissue).

Lesions observed in skin diseases and illnesses of diverse origin, such as *lichen planus*, urticaria, dermatofibroma, psoriasiform dermatitides, and keratoses, are characterized by aberrant integrin expression. CIMs can serve as an agent for the symptomatic treatment of these diseases, being administered topically, intradermally, and subcutaneously at the site of lesions, or in any other appropriate way, when used for this purpose.

Another disease characterized by the formation of cutaneous lesions is psoriasis. Although the etiology of psoriasis attends further elucidation (several viruses and an autoimmune component could be involved), its pathogenesis is associated with abnormal expression of integrins in target tissue (e.g., in vascular cells, keratinocytes, and dendritic cells), proliferation of endothelial and epidermal cells, and an autoimmune component (recruitment of lymphocytes and macrophages to skin and joints). CIMs, therefore, can be used to treat psoriasis in multiple respects.

As a result of their antiviral and anti-inflammatory activity, CIMs are likely to exhibit significant potency in the prevention and treatment of certain diseases with combined etiopathogenesis. As roughly elaborated herein, the term "etiopathogenesis" is used in reference to diseases for which no distinction can be drawn thus far as to the etiology and pathogenesis. In addition to psoriasis, mentioned above, a good example of such a disease is atherosclerosis. A variety of viruses may participate in the development of atherosclerosis. One of the best studied viral contributors is cytomegalovirus, which induces a specific type of infection characterized by plaque formation along the blood vessels (Melnick, J. L., et al., Cytomegalovirus and Atherosclerosis, 17 *BioEssays* 899, 1995). A prominent feature of atherosclerosis is the recruitinent of monocyte-macrophages into atherosclerotic plaques, which is an integrin-dependent process. Also, proliferation of smooth muscle cells, which contributes to the formation of atherosclerotic lesions, is regulated by integrins. As indicated elsewhere in this document, CIMs inhibit the transmission of viral infections virus-to-cell and cell-to-cell. Integrin-mediated adhesion and signaling are also inhibited by CIMs. Thus, CIMs, for multiple reasons, can be used to treat diseases involving combinations of integrin-dependent etiopathogenetic factors, including those that are in part of viral etiology.

Certain neurodegenerative disorders of unclear etiology (e.g., Alzheimer's disease and amyotrophic lateral sclerosis) involve autoimmune inflammation of nervous tissue as a pathogenetic mechanism. CIMs should, therefore, demonstrate significant potency in mitigating the symptoms of these diseases and slowing their progression. This conclusion is further supported by various studies which show that other anti-inflammatory treatments benefit Alzheimer's patients (McGeer, P. L., et al., The Inflammatory Response System of Brain: Implications for *Therapy of Alzheimer's and Other Neurodegenerative Diseases,* 21 *Brain Res. Brain Res. Rev.* 195, 1995; Breitner, J. C., et al., Delayed Onset of Alzheimer's Disease with Nonsteroidal Anti-Inflammatory and Histamine H2 Blocking Drugs, 16 *Neurobiol. Aging* 523, 1995).

To treat or prevent any of these disorders, diseases or conditions, an effective amount of a CIM is administered to an animal in need thereof. Preferably, the animal is a mammal, such as a rabbit, goat, dog, cat, horse or human. Effective dosage forms, modes of administration, and dosage amounts may be determined empirically, and making such determinations is within the skill of the art. It is understood by those skilled in the art that the dosage amount will vary with the disorder, disease or condition to be treated or prevented, the severity of the disorder, disease or other condition, which integrin(s) is (are) to be modulated, the route of administration, the rate of excretion, the duration of the treatment, the identity of any other drugs being administered, the age, size and species of animal, and like factors well known in the arts of medicine and veterinary medicine. In general, a suitable daily dose of a CIM will be that amount of the compound which is the lowest dose effective to produce the desired effect. The effective daily dose of a CIM maybe administered as two, three, four, five, six or more sub-doses, administered separately at appropriate intervals throughout the day. An existing disorder, disease or condition treated with a CIM or combination of CIMs according to the invention may be reduced, inhibited, suppressed or eliminated or one or more symptoms of the disorder, disease or condition may be alleviated or eliminated.

CIMs may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. For instance, the topical application of CIMs to mucous membranes (in the form of creams, gels, suppositories, and other known means of topical administration) can be used to prevent HIV infection of mucosal cells, an important route of HIV transmission. In addition, intralymphatic administration of CIMs may be advantageous in preventing the spread of HIV within the body. Further, CIMs may be administered in conjunction with other treatments for the disorder, disease or condition being treated with the CIM, such as other antiviral drugs, other contraceptives, and other anti-shock or anti-inflammatory drugs or treatments. CIMs maybe encapsulated or otherwise protected against gastric or other secretions, if desired.

While it is possible for a CIM of the invention to be administered alone, it is preferable to administer the CIM as a pharmaceutical formulation (composition). The pharmaceutical compositions of the invention comprise one or more CIMs as an active ingredient in admixture with one or more pharmaceutically-acceptable carriers and, optionally, one or more other compounds, drugs, ingredients and/or materials. Regardless of the route of administration selected, the CIMs of the present invention are formulated into pharmaceutically-acceptable dosage forms by conventional methods known to those of skill in the art. See, e.g., *Remington's Pharmaceutical Sciences* (Mack Publishing Co., Easton, Pa.).

Pharmaceutical carriers are well known in the art (see, e.g., *Remington's Pharmaceutical Sciences* (Mack Publishing Co., Easton, Pa.) and *The National Formulary* (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g, polylactide-polyglycolide, poly (orthoesters), and poly(anhydrides)), elastomeric matrices, liposomes, microspheres, oils (e.g., corn, germ, olive, castor, sesame, cottonseed, and groundnut), cocoa butter, waxes (e.g, suppository waxes), paraffins, silicones, talc, silicylate, etc. Each carrier used in a pharmaceutical composition of the invention must be "acceptable" in the sense of being compatible with the other ingredients of the formulation and not injurious to the animal. Carriers suitable for a selected dosage form and intended route of administration are well known in the art, and acceptable carriers for a chosen CIM, dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the animal. Ingredients and materials suitable for a selected dosage form and intended route of administration are well known in the art, and acceptable ingredients and materials for a chosen CIM, dosage form and method of administration can be determined using ordinary skill in the art.

Pharmaceutical formulations suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulation can be prepared by methods known in the art, e.g, by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Formulations for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Formulations which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more CIMs in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The invention further provides a method of modulating an integrin-mediated function of one or more cells. The method comprises contacting the cell(s) with an amount of a CIM of the invention effective to modulate the integrin-mediated function. Methods of contacting cells in vivo are the same as those described above for treating a disorder, disease or condition. Methods of contacting cells in vitro with compounds (e.g., placed in a solution, such as a cell culture medium, containing the compound) are well known in the art. Suitable conditions (time, temperature, concentrations, type of medium, etc.) are known or can be determined empirically as is well known in the art.

The invention also provides a method of treating a tissue by contacting the tissue with a CIM. Such treatment improves the condition of the tissue for subsequent use, as compared to tissue which is not treated with a CIM. In particular, tissue which is to be transplanted into a recipient may be treated with a CIM, preferably before excision, or, if not, at the time of excision, and the chances of the tissue being successfully transplanted will be increased.

The tissue to be treated maybe any tissue. For instance, the tissue maybe an organ (such as a heart, blood vessel, lung, liver, kidney, skin, cornea, or part of an organ, such as a heart valve), or a non-organ tissue (such as bone marrow, stem cells, or gametes). The tissue is treated by contacting it one or more times with an effective amount of a CIM. Methods of contacting tissues with agents are well known in the art. For instance, the contacting can be accomplished conveniently by rinsing or perfusing the tissue with, and/or submersing the tissue in, a solution of the CIM in a physiologically acceptable diluent. Contacting can also include perfusing the tissue or the donor of the tissue (e.g., a brain-dead human) with a solution of the CM in a physiologically acceptable diluent prior to excision of the tissue. Physiologically-acceptable diluents are those that are compatible with, and not harmful to, the CIM and the tissue. Such diluents are well known and include saline and other solutions and fluids.

Effective amounts of the CIM may be determined empirically, and making such determinations is within the skill of the art. It is understood by those skilled in the art that the amount may vary as a result of one or more factors, including the type and size of the tissue, the intended use of the tissue, the length of storage of the tissue before use, the identity of any other agents being used, the number of treatments, and like factors well known in the art.

The CIM agent may be used in conjunction with other agents to treat tissue. For instance, the tissue may also be treated with preservation agents (i.e., agents which inhibit deterioration of the condition of the tissue), antibiotics, antifungal drugs, antiviral drugs, antiinflammatory drugs, or other treatments (e.g. lung surfactants in the case of lung tissue).

After being contacted with the CIM, the tissue may be used immediately or may be stored until needed. Methods of storing tissue are well known in the art. The tissue may be stored in contact with the CIM. Tissues are preferably stored at low temperatures, typically 4–18° C., and non-organ tissues may typically be frozen. The time of storage will vary depending on the type of tissue, the storage environment (including the temperature of storage), and the intended use. Such times can be determined empirically, and making such determinations is within the skill in the art. Regardless of the length and conditions of storage, timely treatment with a CIM mitigates the effects of harvest and/or storage, and treated tissues will be in better condition than tissues not treated with a CIM.

Tissues treated with CIMs may be used for a variety of purposes. For instance, they may be transplanted into recipients. They may also be used for research purposes, such as studying the function of the tissue.

It is taken that CIMs may induce a rest state in tissue, which lasts until the CIMs are removed. In addition, treatment of a tissue with an CIM improves the condition of the tissue by reducing the negative effects and consequences of harvesting and storing tissue. For instance, CIMs inhibit (prevent or reduce) the adhesion and aggregation of cells which would otherwise cause injury to a tissue (see the discussion above). Thus, treatment of a tissue with a CIM prevents or reduces damage to the tissue.

In particular, ischemia (anemia due to constriction or obstruction of a blood vessel) occurs upon harvesting an organ. Both the injury due to ischemia and that due to reperfusion after ischemia (which generally occurs upon resuming blood flow in an organ, such as that occurring when transplanting an organ into a recipient), can be inhibited by treatment of the organ with a CIM. To achieve maximum inhibition of ischemic injury and ischemic reperfusion injury, the organ should be contacted with the CIM before or immediately after harvesting of or interruption of normal blood supply to the organ, to mitigate the rapid onset of injury and other changes associated with ischemic injury. Such treatment has beneficial effects even for organs that are to be used immediately, such as in the case of many transplants. Preferably, the contacting takes place by perfusing the organ with a solution comprising the CIM.

For organs that are stored (even for a short time), benefits are obtained by contacting the organ with a CIM immediately prior to use. This treatment may serve, among other purposes, to eliminate the effects of an), cytokines that may have been produced, as well as to prevent adhesion and aggregation of cells which would otherwise cause tissue injury. The treatment of an organ after storage can be the first treatment of the organ with a CIM, or can be the second treatment of an organ which was first treated before or immediately after harvest. Again, the organ is preferably treated by perfusion with a solution comprising the CIM.

As discussed above, CIMs suppress undesired immune responses. Thus, treatment of a tissue with a CIM prior to transplantation acts as an initial treatment for the prevention of graft rejection and/or graft versus host disease (GVHD) in transplant recipients.

Of course, the recipient may receive additional amounts of an CIM to prevent graft rejection and/or GVHD as described above. The amount administered to the recipient should also be chosen so that inhibition of injury due to ischemia and ischemia reperfusion is continued.

Finally, CIMs can inhibit the transmission of viral infections from a tissue to a recipient of transplanted tissue and vice versa (see the discussion above). This includes all of the viral infections described above.

The invention also provides a kit for treating tissues. The kit is a packaged combination of one or more containers holding reagents and other items useful for treating tissues according to invention. The kit comprises a container holding a CIM. Suitable containers include bottles, bags, vials, test tubes, syringes, and other containers known in the art. The kit may also contain other items which are known in the art or which may be desirable from a commercial and user standpoint, such as instructions for treating a tissue, a container for the tissue, diluents, preservation agents, antibiotics, antifungal drugs, antiviral drugs, anti-inflammatory drugs, surfactants, buffers, empty syringes, tubing, gauze, pads, disinfectant solution, etc.

It should be understood that, whereas some integrin functions are modulated by CIMs of formula (2), there may be certain integrin functions, the modulation of which is achieved by the other three ajoene enantiomers of instant invention and derivatives thereof. Thus, all integrin-modulating substances incorporating the corresponding trithia oxide chiral structures should be properly referred to as CIMs.

EXAMPLES

Example 1

Methods of Ajoene Separation into Four Enantiomers

A 3:1 mixture of racemic Z- and E-ajoenes (unseparated ajoene) was dissolved in heptane/ethanol/diethylamine (90:10:0.1) and separated by HPLC on a 4.6×250 mm Chiralpak AS column (Chiral Technologies, Exton, Pa.) using a mobile phase of heptane/ethanol/diethylainine 90:10:0.1 (flow rate, 1 mL/min; temperature, 25° C.). The detector recorded two parameters: the absorption of the eluate at 254 nm and the rotation of the plane of polarization of polarized light passing through the eluate; in the latter case, upward and downward peaks corresponded, respectively, to dextrorotatory (+) and levorotatory (−) enantiomers. The resulting chromatogram contained eight peaks superimposed in such a way that four pairs were clearly seen. In each pair, the two coinciding peaks correspond to a particular enantiomer of ajoene, i.e., Z(+), Z(−), E(+), and E(−). The Z(+), E(+), E(−), and Z(−) enantiomers of ajoene were eluted with retention times of 21.4, 23.8, 26.2, and 33.1 minutes, respectively.

In another experiment, the separation was achieved in the same system, the only difference being in the composition of the mobile phase (hexane/ethanol 90:10). Again, the Z(+), E(+), E(−), and Z(−) enantiomers were clearly separated (the respective elution times were 20.4, 23.1, 24.6, and 31.2 minutes). The peaks were collected into tared polypropylene tubes and stored on ice for 48 hours, after which analytical runs were performed with each fraction. The results of the analysis demonstrated that very good separation of the isomers had been achieved (~98%) and that the isomers did not undergo racemization under the conditions of the storage. Thereafter, the fractions were dried down by rotary evaporation (6 to 10 min at 35° C.) and re-analyzed under the same conditions. The peaks present in the fractions showed their original retention times and no other peaks were present. Thus, the drying down process did not cause racemization.

In a yet another experiment, HPLC separation of the enantiomers involved a different column (10×250 mm Chiralpak AD). The conditions used were as follows: mobile phase, hexane/ethanol 90:10; flow rate, 6 mL/min; temperature, ambient; detector wavelength, 254 nm. Typically, 10 mg of the 3:1 mixture was loaded per run and fractions collected manually. The fractions were dried down by rotary evaporation at 37° C., resulting in light oil. The oil was taken up in anhydrous ether and dried down by rotary evaporation. The resulting light oils were stored at −80° C. in sealed containers. Analytical runs on the same column demonstrated that Z(+), E(+), E(−), and Z(−) enantiomers of ajoene had retention times of 53 min, 58 min, 62 min, and 75 min.

Example 2

Inhibition of VLA-4- mediated Cell Adhesion: A Method of Assessment of Integrin-modulating Activity of the Four Enantiomers of Ajoene Integrin-modulating activity of the enantiomers was compared in a well-defined system of inhibition of VLA-4-mediated adhesion of enzyme-labeled PM1 cells (NIH AIDS Repository, Rockville, Md.) to VCAM-1-coated artificial substrata. In this experiment, enzyme-linked immunosorbent assay (ELISA) plates were coated with rabbit anti-human IgG (Fc-specific). Aliquots of 100 μL of supernatant from VCAM/IgG-secreting COS7 cells were added to each well, the plates incubated at 37° C. for 1 hour, and the wells washed with phosphate-buffered saline (PBS). Thereafter, 50 μL aliquots of the enantiomers (various dilutions in RPMI 1640 medium) were introduced to each well, followed by addition of 50 μL PM1 cells ($4 \times 10^6$ per mL) labeled with horseradish peroxidase (HRP) by pinocytosis. The plates were incubated at room temperature for 10 min, centrifuged (1000 rpm, 1 min) and incubated once again at 37° C. for additional 10 min. Cells that failed to form VLA-4-dependent adhesive contacts with the substratum were washed off with PBS in two turns. Adherent cells were lyzed by adding to each well a buffered solution of the substrate, supplemented with 1% Triton X-100. The reaction was stopped with 0.5 M $H_2SO_4$, and the optical density of the wells, read at 450 nm. The value of this parameter, characterizing the activity of the enzyme and the number of the adherent cells, is inversely proportional to the integrin-modulating activity of the compound.

The Z(−) enantiomer of ajoene consistently exhibited a 4-fold higher adhesion-inhibiting activity than any other enantiomer of the original 3:1 mixture of racemic Z- and E-ajoenes.

Example 3

Differential Inhibition by Ajoene Enantiomers of Integrin-dependent Fusion Leading to Syncytium Formation in HIV-infected Cells The purified enantiomers were taken up in DMSO at a concentration of 10 mg/mL. Dilutions were made in RPMI 1640 medium containing 10% fetal calf serum and 10 mM HEPES (cRPMI). H9 cells (ATCC, Rockville, Md.) infected with HIV-1$_{RF}$ (NIH AIDS Repository, Rockville, Md.) and uninfected H9 cells were washed with cRPMI and resuspended in cRPMI at a density of $4 \times 10^6$ per mL. Uninfected cells (50 μL) were mixed with serial dilutions of the compounds (100 μL) and incubated at 37° C. for 30 min before adding and mixing 50 μL of infected H9 cells. The plates were incubated at 37° C. for 6 to 15 hours before scoring syncytium formation.

The results are presented in FIG. 1. As shown in FIG. 1, the Z(−) enantiomer was at least four times more active than its Z(+) counterpart, racemic E-ajoene, or the unseparated 3:1 mixture of racemic Z- and E-ajoenes (the respective values of IC$_{100}$ were 12.5 and 50 micromoles per liter). A similar result was obtained in another system, where syncytium formation was induced by mixing and incubating together for 13 hours 50 μl MT2 cells (NIH AIDS Repository) and 50 μl U937 cells (ATCC) infected with HIV-1$_{RF}$ (both cell populations had the density of $2 \times 10^6$ per mL).

Taken together, Examples 2 and 3 demonstrate that Z(−)-4,5,9-trithiadodeca-1,6,11-triene-9-oxide is a stereo selective, chiral integrin modulator, the activity of which is significantly higher than that of the parent racemates (E-, Z-ajoenes, and various mixtures thereof).

We claim:

1. A compound of the formula:

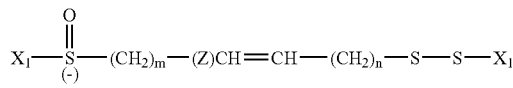

(2)

wherein:
each $X_1$ may be the same or different than the other $X_1$ and each $X_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

2. A pharmaceutical composition comprising a pharmaceutically-acceptable carrier and a compound of the formula:

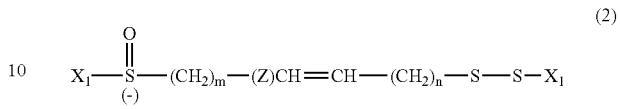

(2)

wherein:
each $X_1$ may be the same or different than the other $X_1$ and each $X_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

3. A enantiomer of ajoene selected from the group consisting of:
Z(−)-4,5,9-trithiadodeca-1,6,11-triene-9-oxide;
Z(+)-4,5,9-trithiadodeca-1,6,11-triene-9-oxide;
E(−)-4,5,9-trithiadodeca-1,6,11-triene-9-oxide; and
E(+)-4,5,9-trithiadadeca-1,6,11-triene-9-oxide.

4. A method of modulating an integrin-mediated function of one or more cells comprising contacting the cell(s) with an amount of a compound of the following formula effective to modulate the integrin-mediated function:

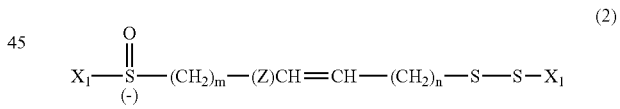

(2)

wherein:
each $X_1$ may be the same or different than the other $X_1$ and each $X_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

5. The method of claim 4 wherein the function is adhesion, migration, aggregation, signaling, fusion, internalization, or a combination of one or more of these functions.

6. The method of claim 5 wherein the aggregation of platelets is inhibited.

7. The method of claim 5 wherein the migration, adhesion, or aggregation of neutrophils is inhibited.

8. A method of treating or preventing a disorder, disease or condition in which one or more integrins play a role comprising administering to an animal in need thereof an effective amount of a compound of the following formula:

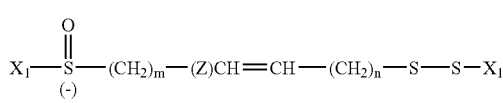

(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more tower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

9. A method of treating a thrombotic disorder or a disease or condition arising therefrom comprising administering to an animal in need thereof an effective amount of a compound of the following formula:

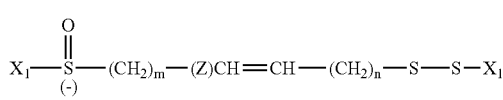

(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

10. The method of claim 9 wherein the disease or condition is ischemia, myocardial infarction or stroke.

11. A method of treating shock comprising administering to an animal in need thereof an effective amount of a compound of the following formula:

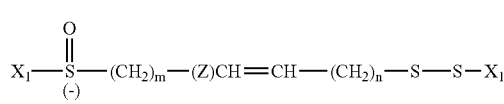

(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula ROON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

12. The method of claim 11 wherein the compound is Z(-)-4,5,9-trithiadodeca-1,6,11-triene-9-oxide.

13. A method of treating inflammation or an inflammatory disease comprising administering to an animal in need thereof an effective amount of a compound of the following formula:

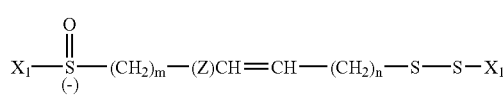

(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

14. The method of claim 13 wherein the inflammation is associated with peritonitis, meningitis, reperfusion after ischemia, delayed type hypersensitivity, an Arthus reaction, anaphylaxis, allograft rejection, graft-versus-host disease, or arthritis.

15. A method of treating, or inhibiting the transmission of a viral infection comprising administering to an animal in need thereof an effective amount of a compound of the following formula:

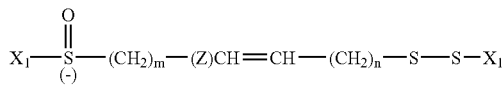
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

16. The method of claim 15 wherein the viral infection is caused by a virus, the transmission of which involves fusion of at least a part of the virus with the membrane of the cell that is to be infected, and the compound inhibits the fusion of the virus with the cell membrane.

17. The method of claim 16 wherein the viral infection is caused by a virus which is an enveloped virus.

18. The method of claim 17 wherein the viral infection is caused by a virus of the Retroviridae family, Hepadnaviridae family, Orthomyxoviridae family, Flaviviridae family, Togaviridae family, Paramyxoviridae family, Rhabdoviridae family, Poxviridae family or Herpesviridae family.

19. The method of claim 18 wherein the viral infection is caused by a virus of the Retroviridae family.

20. The method of claim 19 wherein the Retroviridae is HIV.

21. The method of claim 16 wherein the viral infection is caused by a virus of the Adenoviridae family, Picornaviridae family, Rotaviridae family or the Papovaviridae family.

22. A method of treating arthritis comprising administering to an animal in need thereof an effective amount of a compound of the following formula:

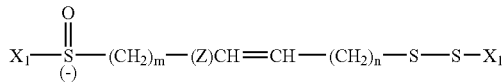
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

23. A method of treating or suppressing an adverse, undesirable or self-destructive immune response comprising administering to an animal in need thereof an effective amount of a compound of the following formula:

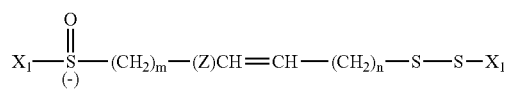
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula $RSO_2$—, a group of the formula RSO—, a group of the formula $RSO_2O$—, a group of the formuis RSOO—, a halogen atom, ammonia, nitrozo, nitro, mercapto, or sulfo;
R is hydrogen, lower alkyl, aryl, or an aryl substituted with one or more lower alkyls;
m is 0–30; and
n is 0–30.

24. The method of claim 23 wherein immune response is an allergic reaction.

25. The method of claim 24 wherein the allergic reaction is delayed type hypersensitivity, an Arthus reaction or anaphylaxis.

26. The method of claim 23 wherein the immune response is allograft rejection or graft-yersus-host disease.

27. A method of treating an autoimmune disease comprising administering to an animal in need thereof an effective amount of a compound of the following formula:

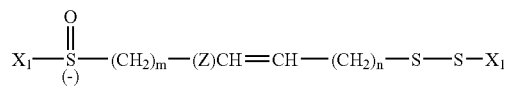
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

28. The method of claim 27 wherein the autoimmune disease is rheumatoid arthritis, systemic lupus erythematosus, Sjogren's syndrome, multiple sclerosis, insulin-dependent diabetes mellitus, glomerulonephritis, Graves disease, Hashimoto's thyroiditis, or vasculitides.

29. A method of treating psoriasis comprising administering to an animal in need thereof an effective amount of a compound of the following formula:

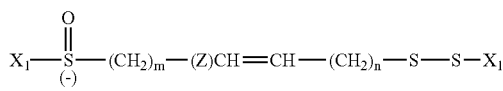

(2)

wherein:
each X$_1$ may be the same or different than the other X$_1$ and each X$_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula (R)$_2$N—, a group of the formula RCON—, a group of the formula RN═N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

30. A method of treating artherosclerosis comprising administering to an animal in need thereof an effective amount of a compound of the following formula:

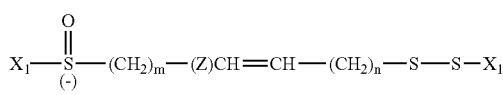

(2)

wherein:
each X$_1$ may be the same or different than the other X$_1$ and each X$_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula (R)$_2$N—, a group of the formula RCON—, a group of the formula RN═N—, a group of the formula RS—, a group of the formula RSO$_2$—, a group of the formula RSO—, a group of the formula RSO$_2$O—, a group of the formula RSOO—, a halogen atom, ammonio, nitrozo, nitro, meroapto, or sulfo;

R is hydrogen, lower alkyl, aryl, or an aryl substituted with one or more lower alkyls;

m is 0–30; and n is 0–30.

31. A method of treating a disorder, disease or condition involving a plurality of integrin-dependent mechanisms wherein the disorder, disease, or condition is selected from the group consisting of a thrombotic disorder or disease, shock, inflammation, inflammatory disease, viral infection, arthritis, autoimmune disease, psoriasis, atherosclerosis, tumor metastasis, fertilization, cell-cell fusion, lesion formation, transfer of genetic information, and combinations thereof comprising administering to an animal in need thereof an effective amount of a compound of the following formula:

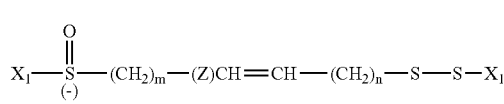

(2)

wherein:
each X$_1$ may be the same or different than the other X$_1$ and each X$_1$ is hydrogen, an alkyl, an alkenyl, an alkynyl, an aryl, an aryl substituted with one or more —NO$_2$ groups, an aryl substituted with one or more lower alkyls, a group of the formula RO—, a group of the formula RCO—, a group of the formula RCOO—, a group of the formula ROCO—, a group of the formula (R)$_2$N—, a group of the formula RCON—, a group of the formula RN═N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;

m is 0–30; and n is 0–30.

32. A method of inhibiting metastasis of tumors, or inhibiting integrin-mediated carcinogenesis comprising administering to an animal in need thereof an effective amount of a compound of the following formula:

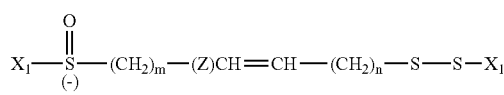

(2)

wherein:
each X$_1$ may be the same or different than the other X$_1$ and each X$_1$ is hydrogen, an alkyl, an alkenyl, an alkynyl, an aryl, an aryl substituted with one or morn —NO$_2$ groups, an aryl substituted with one or more lower alkyls, a group of the formula RO—, a group of the formula RCO—, a group of the formula RCOO—, a group of the formula ROCO—, a group of the formula (R)$_2$N—, a group of the formula RCON—, a group of the formula RN═N—, a group of the formula RS—, a group of the formula RSO$_2$—, a group of the formula RSO—, a group of the formula RSO$_2$O—, a group of the formula RSOO—, a halogen atom, ammonio, nitrozo, nitro, mercapto, or sulfo;

R is hydrogen, lower alkyl, aryl, or an aryl substituted with one or more lower alkyls;
m is 0–30; and
n is 0–30.

33. A method of contraception comprising administering to an animal in need thereof an effective amount of a compound of the following formula:

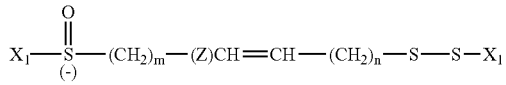
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

34. A method of inhibiting undesirable integrin-mediated cell-cell fusion comprising administering to an animal in need thereof an effective amount of a compound of the following formula:

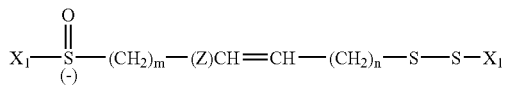
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, meroapto, or sulfo;
R is hydrogen, lower alkyl, aryl, or an aryl substituted with one or more lower alkyls;
m is 0–30; and
n is 0–30.

35. The method of claim 34 wherein the undesired cell-cell fusion is cell-cell fusion that results in the formation of multinucleate cells or multinucleate germinal cells.

36. The method of claim 35 wherein the multinucleate cells are syncytia, giant cells, or osteoclasts.

37. A method of inhibiting the formation of a lesion comprising administering to an animal in need thereof an effective amount of a compound of the following formula:

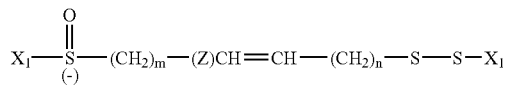
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

38. The method of claim 37 wherein the lesion is a granuloma.

39. The method of claim 37 wherein the lesion is a fibrotic lesion.

40. A method of inhibiting the transfer of genetic material comprising administering to an animal in need thereof an effective amount of a compound of the following formula:

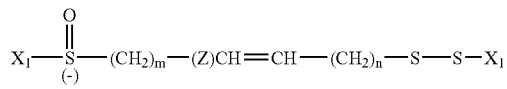
(2)

wherein:
each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower aikyls, a group of the formula RO—, a group of the formula RCO—, a group of the formula RCOO—, a group of the formula ROCO—, a group of the formula $(R)_2N$—, a group of the formula RCON—, a group of the formula RN=N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
R is hydrogen, lower alkyl, aryl, or an aryl substituted with one or more lower alkyls;
m is 0–30; and
n is 0–30.

41. The method of claim 40 wherein the genetic material is viral genetic material.

42. A method of treating a tissue in order to inhibit degradataion thereof comprising contacting the tissue with an effective amount of a compound of the following formula:

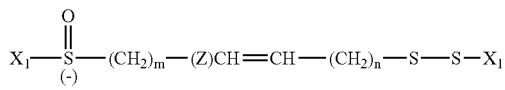 (2)

wherein:
 each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
 R is hydrogen lower alkyl, aryl, or an aryl substituted with one or more lower alkyls;
 m is 0–30; and
 n is 0–30.

43. The method of claim 42 wherein the tissue is excised from a donor and subsequently transplanted into a recipient.

44. The method of claim 43 wherein the tissue is treated with the compound before excision, at the time of excision, after excision, or combinations thereof.

45. The method of claim 43 wherein the tissue is stored in contact with the compound.

46. The method of claim 42 wherein the tissue is an organ.

47. The method of claim 46 wherein the organ is a heart, a blood vessel, a lung, a liver, a kidney, skin, or a cornea.

48. The method of claim 46 wherein the organ is perfused with a solution comprising the compound.

49. The method of claim 42 wherein the tissue is part of an organ.

50. The method of claim 49 wherein the part of an organ is a heart valve.

51. The method of claim 42 wherein the tissue is a non-organ tissue.

52. The method of claim 51 wherein the non-organ tissue is bone marrow, stem cells, or gametes.

53. The method of claim 43 wherein an effective amount of the compound is administered to the recipient of the tissue at the time of receiving the tissue, at one or more times after receiving the tissue or both.

54. A kit for treating a tissue comprising a container holding a compound of the following formula:

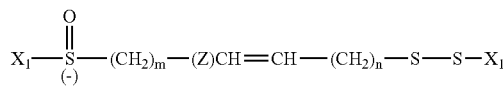 (2)

wherein:
 each $X_1$ may be the same or different than the other $X_1$ and each $X_1$ is hydrogen, an alkyl, an alkenyl, an alkynyl, an aryl, an aryl substituted with one or more —$NO_2$ groups, an aryl substituted with one or more lower alkyls, a group of the formula RO—, a group of the formula RCO—, a group of the formula RCOO—, a group of the formula ROCO—, a group of the formula $(R)_2N$—, a group of the formula RCON—, a group of the formula RN═N—, a group of the formula RS—, a group of the formula $RSO_2$—, a group of the formula RSO—, a group of the formula $RSO_2O$—, a group of the formula RSOO—, a halogen atom, ammonio, nitrozo, nitro, mercapto, or sulfo;
 R is hydrogen, lower alkyl, aryl, or an aryl substituted with one or more lower alkyls;
 m is 0–30; and
 n is 0–30.

* * * * *